US009624551B2

(12) United States Patent
Li et al.

(10) Patent No.: US 9,624,551 B2
(45) Date of Patent: Apr. 18, 2017

(54) CATALYTIC NUCLEIC ACID PROBES AS MICROBIAL INDICATORS

(75) Inventors: Yingfu Li, Dundas (CA); M. Monsur Ali, Hamilton (CA); Sergio D. Aguirre, Bolton (CA)

(73) Assignee: McMaster University, Hamilton, ON (CA)

( * ) Notice: Subject to any disclaimer, the term of this patent is extended or adjusted under 35 U.S.C. 154(b) by 248 days.

(21) Appl. No.: 14/003,645

(22) PCT Filed: Mar. 8, 2012

(86) PCT No.: PCT/CA2012/000205
§ 371 (c)(1),
(2), (4) Date: Sep. 6, 2013

(87) PCT Pub. No.: WO2012/119231
PCT Pub. Date: Sep. 13, 2012

(65) Prior Publication Data
US 2014/0005072 A1   Jan. 2, 2014

Related U.S. Application Data

(60) Provisional application No. 61/450,169, filed on Mar. 8, 2011.

(51) Int. Cl.
C07H 21/04     (2006.01)
C12Q 1/68      (2006.01)
C12N 15/11     (2006.01)

(52) U.S. Cl.
CPC .......... *C12Q 1/689* (2013.01); *C12Q 1/6804* (2013.01); *C12Q 1/6811* (2013.01); *C12Q 1/6816* (2013.01); *C12N 15/111* (2013.01); *C12N 2310/127* (2013.01); *C12N 2310/3517* (2013.01); *C12N 2320/11* (2013.01); *C12N 2330/31* (2013.01)

(58) Field of Classification Search
None
See application file for complete search history.

(56) References Cited

U.S. PATENT DOCUMENTS

| 2010/0015608 A1* | 1/2010 | Kolpashchikov .... C12Q 1/6816 435/6.11 |
| 2011/0143338 A1* | 6/2011 | Todd ...................... C12N 15/111 435/6.1 |

OTHER PUBLICATIONS

Ali, M.M et al., Fluorogenic DNAzyme probes as bacterial indicators. Angew Chem Intl Ed Engl, Apr. 11, 2011; vol. 50(16), p. 3751-3754.
Liu, J. et al. Improving fluorescent DNAzyme biosensors by combining inter-and intramolecular quenchers. Analytic Chemistry, Dec. 1, 2003, vol. 75(23), p. 6666-6672.
Laczka, O. et al. Pathogen detection: A perspective of traditional methods and biosensors. Biosensors and Bioelectronics. Feb. 15, 2007, vol. 22(7), p. 1205-17.
Velusamy, V. et al. An overview of foodborne pathogen detection: In the perspective of biosensors, Biotechology Advances. 2010, V 28, p. 232-254.
Wright, A.C. et al. Pathogens in raw foods: what the salad bar can learn from the raw bar. Current Opinions in Biotechnology. 2009, V 20, p. 172-177.
Call, D.R., Challenges and Opportunities for Pathogen Detection Using DNA Microarrays. Critical Reviews in Microbiology, 2005, V 31, p. 91-99.
Yagi, K., Applications of whole-cell bacterial sensors in biotechnology and environmental science. Appl. Microbiol. Biotechnol. 2007, V 73, p. 1251-1258.
Navani, N.K., et al. Nucleic acid aptamers and enzymes as sensor. Current Opinions in Chemical Biology. 2006, V 10, p. 272-281.
Liu, J. et al. Functional Nucleic Acid Sensors. Chem. Rev. 2009, V 109, No. 5, p. 1948-1998.
Fang, X. et al. Aptamers Generated from Cell-SELEX for Molecular Medicine: A Chemical Biology Approach. Accounts of Chemical Research. 2010, V 43, No. 1, p. 48-57.
Breaker, R.R., et al. A DNA enzyme that cleaves RNA. Chem. Biol. 1994 V 1, p. 223-229.
Cuenoud, B, et al. A DNA metalloenzyme with DNA ligase activity. Nature, 1995, V 375, p. 611-614.
Chinnapen, D., A deoxyribozyme that harnesses light to repair thymine dimers in DNA, Proc. Natl. Acad. Sci. USA 2004, V 101, No. 1, p. 65-69.
Schlosser, K., et al. Biologically Inspired Synthetic Enzymes Made from DNA. Chemistry and Biology. 2009. V 16, p. 311-322.
Silverman, S.K., DNA as a Versatile Chemical Component for Catalysis, Encoding, and Stereocontrol. Angew. Chem. Int. Ed. 2010, V 49, p. 7180-7201.
Tuerk, C., et al., Systematic Evolution of Ligands by Exponential Enrichment: RNA Ligands to Bacteriophage T4 DNA Polymerase, Science, 1990, V 249, p. 505-510.
Ellington, A.D., et al. In vitro selection of RNA molecules that bind specific ligands, Nature, 1990, V 346, p. 818-822.
Joyce, G. F. Forty Years of in Vitro Evolution. Angew. Chem. Int. Ed. 2007, V 46, p. 6420-6436.
Liu, J., et al. Acelerated color change of gold nanoparticles assembled by DNAzymes for simple and fast colorimetric Pb2+ detection. J. Am. Chem. Soc. 2004, V 126, p. 12298-122305.
Liu, J., et al. Rational Design of "Turn-on" Allosteric DNAzyme Catalytic Beacons for Aqueous Mercury Ions with Ultrahigh Sensitivity and Selectivity. Angew. Chem. Int. Ed. 2007, V 46, p. 7587-7590.
Hollenstein, H., et al. A Highly Selective DNAzyme Sensor for Mercuric Ions. Angew. Chem. Int. Ed. 2008, V 47, p. 4346-4350.
Lund, K., et al. Molecular robots guided by prescriptive landscapes, Nature 2010, V 465, p. 206-210.

(Continued)

*Primary Examiner* — David Thomas
(74) *Attorney, Agent, or Firm* — Bereskin & Parr LLP/S.E.N.C.R.L., s.r.l.; I. Laurence MacPhie; Ainslie Parsons

(57) ABSTRACT

The disclosure relates to a method of generating catalytic nucleic acid probes useful for detecting microorganisms such as bacterial pathogens. In one embodiment, the catalytic nucleic acid probes are fluorogenic DNAzymes. The disclosure also relates to catalytic nucleic acid probes and methods of using the probes for detecting microorganisms.

17 Claims, 13 Drawing Sheets

(56) References Cited

OTHER PUBLICATIONS

Mei, S., et al. An Efficient RNA-Cleaving DNA Enzyme that Synchronizes Catalysis with Fluorescence Signaling. J. Am. Chem. Soc. 2003, V 125, p. 412-420.

Liu, Z. et al. Assemblage of Signaling DNA Enzymes with Intriguing Metal-Ion Specificities and pH Dependences. J. Am. Chem. Soc. 2003, V 125, p. 7539-7545.

Kandadai, S.A., et al. Characterization of a catalytically efficient acidic RNA-cleaving deoxyribozyme. Nucleic Acids Res. 2005, V 33, No. 22, p. 7164-7175.

Shen, Y., et al. Characterizing the Secondary Structure and Identifying Functionally Essential Nucleotides of pH6DZ1, a Fluorescence-Signaling and RNA-Cleaving Deoxyribozyme, Biochemistry 2005, V 44, p. 12066-12076.

Chiuman, W., et al. Revitalization of Six Abandoned Catalytic DNA Species Reveals a Common Three-way Junction Framework and Diverse Catalytic Cores. J. Mol. Biol. 2006, V 357, p. 748-754.

Chiuman, W., et al. Evolution of High-Branching Deoxyribozymes from a Catalytic DNA with a Three-Way Junction. Chem, Biol. 2006, V 13, p. 1061-1069.

Ali, M. M., et al. Evolution of High-Branching Deoxyribozymes from a Catalytic DNA with a Three-Way Junction. Can. J. Chem. 2007, V 85, p. 261-273.

Chiuman, W., et al. Simple Fluorescent Sensors Engineered with Catalytic DNA 'MgZ' Based on a Non-Classic Allosteric Design. PL0S One 2007, V 2, Issue 11, p. e1224.

Kandadai, S.A., et al. Characterization of an RNA-Cleaving Deoxyribozyme with Optimal Activity at pH 5. Biochemistry, 2009, V 48, p. 7383-7391.

Shen, Y., et al. Catalysis and Rational Engineering of trans-Acting pH6DZ1, an RNACleaving and Fluorescence-Signaling Deoxyribozyme with a Four-Way Junction Structure. Chem. Bio. Chem. 2006, V 7, p. 1343-1348.

Rupcich, N., et al., Quenching of Fluorophore-Labeled DNA Oligonucleotides by Divalent Metal Ions: Implications for Selection, Design, and Applications of Signaling Aptamers and Signaling Deoxyribozymes. J. Am. Chem. Soc. 2006, V 128, p. 780-790.

Shen, Y., et al. Entrapment of Fluorescence Signaling DNA Enzymes in Sol-Gel-Derived Materials for Metal Ion Sensing. Anal. Chem. 2007, V 79, p. 3494-3503.

Li, Y., et al. Kinetics of RNA Degradation by Specific Base Catalysis of Transesterification Involving the 2¢-Hydroxyl Group. J. Am. Chem. Soc. 1999, V 121, p. 5364-5372.

Liu, J. et al. Fluorescent DNAzyme biosensors for met al ions based on catalytic molecular beacons. Methods of Molecular Biology, 2006, vol. 335 (VII), pp. 275-288.

International Search Report and Written Opinion for PCT/CA2012/000205 dated Jun. 11, 2012.

* cited by examiner a) RFD-EC1
5' CACGGATCCT GACAAGGATG TGTGCGTTGT CGAGACCTGC GACCGGAACA
  CTACACTGTG TGGGATGGAT TTCTTTACAG TTGTGTGCAG CTCCGTCCGA
  CTCTTCCTAG CFRQGGTTCG ATCAAGA
RFSS1
5' CACGCTGTAC GGATGGAGTC GCGAGCCTGC GACCGGAAAT GAAAGATCTT
  TCGCGTTTTG CTCATGCGAT GGATTTTTTA CAGTGGGCAG CTCCGTCCGA
  CTCTTCCTAG CFRQGGTTCG ATCAAGA
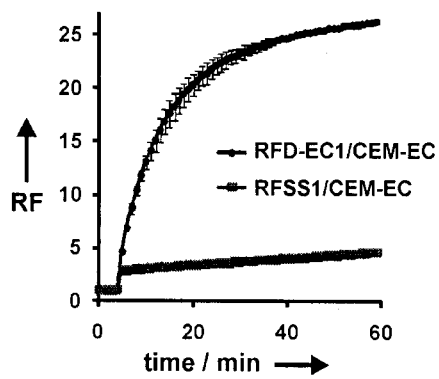
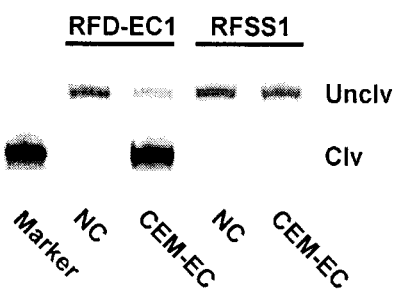
FIGURE 3

A % cleavage= clv$_{TC}$- clv$_{CC}$

B

| | | Temperature | | | | |
|---|---|---|---|---|---|---|
| RC1 | | 4 | 15 | 23 | 37 | 50 |
| clv (%) | | 27 | 58 | 53 | 7* | 7* |

Mk CC TC
— — ←unclv
— — ←clv

C

| | pH | | | | | | | | |
|---|---|---|---|---|---|---|---|---|---|
| RC2 | 5.0 | 5.5 | 6.0 | 6.5 | 7.0 | 7.5 | 8.0 | 8.5 | 9.0 |
| clv (%) | 7 | 8 | 11 | 21 | 27 | 39 | 40 | 21 | 5 |

D

| | Ratio (FS1:EC1T) | | | | | | | |
|---|---|---|---|---|---|---|---|---|
| RC1 | 1:0 | 1:1 | 1:2 | 1:5 | 1:10 | 1:25 | 1:50 | 1:100 |
| clv (%) | 0 | 7 | 5 | 11 | 22 | 33 | 45 | 44 |

FIGURE 14

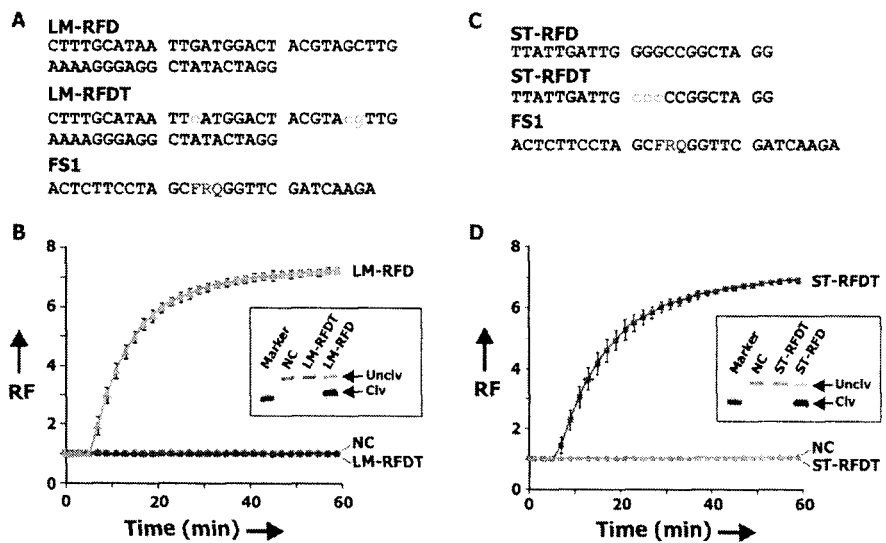

A LM-RFD
CTTTGCATAA TTGATGGACT ACGTAGCTTG
AAAAGGGAGG CTATACTAGG

LM-RFDT
CTTTGCATAA TT ATGGACT ACGTA TTG
AAAAGGGAGG CTATACTAGG

FS1
ACTCTTCCTA GCFRQGGTTC GATCAAGA

C ST-RFD
TTATTGATTG GGGCCGGCTA GG

ST-RFDT
TTATTGATTG CCGGCTA GG

FS1
ACTCTTCCTA GCFRQGGTTC GATCAAGA

FIGURE 15

SEQUENCE LISTING

```
<160> NUMBER OF SEQ ID NOS: 17

<210> SEQ ID NO 1
<211> LENGTH: 98
<212> TYPE: DNA
<213> ORGANISM: Artificial Sequence
<220> FEATURE:
<223> OTHER INFORMATION: Synthetic Construct (EC1)

<400> SEQUENCE: 1
cacggatcct gacaaggatg tgcgttgtcg agacctgcga ccggaacact acactgtgtg      60
gggatggatt tctttacagt tgtgtgcagc tccgtccg                             98

<210> SEQ ID NO 2
<211> LENGTH: 70
<212> TYPE: DNA
<213> ORGANISM: Artificial Sequence
<220> FEATURE:
<223> OTHER INFORMATION: Synthetic Construct (EC1T-RFD)

<400> SEQUENCE: 2
gatgtgcgtt gtcgagacct gcgaccggaa cactacactg tgtggggatg gatttcttta      60
cagttgtgtg                                                            70
```

<210> SEQ ID NO 3
<211> LENGTH: 50
<212> TYPE: DNA
<213> ORGANISM: Artificial Sequence
<220> FEATURE:
<223> OTHER INFORMATION: Synthetic Construct (LM-RFD)

<400> SEQUENCE: 3
ctttgcataa ttgatggact acgtagcttg aaaagggagg ctatactagg        50

<210> SEQ ID NO 4
<211> LENGTH: 22
<212> TYPE: DNA
<213> ORGANISM: Artificial Sequence
<220> FEATURE:
<223> OTHER INFORMATION: Synthetic Construct (ST-RFD)

<400> SEQUENCE: 4
ttattgattg gggccggcta gg                                       22

<210> SEQ ID NO 5
<211> LENGTH: 28
<212> TYPE: DNA
<213> ORGANISM: Artificial Sequence
<220> FEATURE:
<223> OTHER INFORMATION: Synthetic Construct (FS1)
<220> FEATURE:
<221> NAME/KEY: misc_feature
<222> LOCATION: (13)..(13)
<223> OTHER INFORMATION: n=fluorescein-dT
<220> FEATURE:
<221> NAME/KEY: misc_feature
<222> LOCATION: (14)..(14)
<223> OTHER INFORMATION: n=riboadenosine
<220> FEATURE:
<221> NAME/KEY: misc_feature
<222> LOCATION: (15)..(15)
<223> OTHER INFORMATION: n=dabcyl-dT

<400> SEQUENCE: 5
actcttccta gcnnnggttc gatcaaga                                 28

<210> SEQ ID NO 6
<211> LENGTH: 16
<212> TYPE: DNA
<213> ORGANISM: Artificial Sequence
<220> FEATURE:
<223> OTHER INFORMATION: Synthetic Construct (FP1)

<400> SEQUENCE: 6
cacggatcct gacaag                                              16

<210> SEQ ID NO 7
<211> LENGTH: 12
<212> TYPE: DNA
<213> ORGANISM: Artificial Sequence
<220> FEATURE:
<223> OTHER INFORMATION: Synthetic Construct (RP1)

<400> SEQUENCE: 7
cggacggagc tg                                                  12

<210> SEQ ID NO 8
<211> LENGTH: 32
<212> TYPE: DNA
<213> ORGANISM: Artificial Sequence
<220> FEATURE:

```
<223> OTHER INFORMATION: Synthetic Construct (RP2)
<220> FEATURE:
<221> NAME/KEY: misc_feature
<222> LOCATION: (21)..(21)
<223> OTHER INFORMATION: n=hexaethyleneglycol spacer

<400> SEQUENCE: 8
aaaaaaaaaa aaaaaaaaaa ncgacggagc tg                              32

<210> SEQ ID NO 9
<211> LENGTH: 23
<212> TYPE: DNA
<213> ORGANISM: Artificial Sequence
<220> FEATURE:
<223> OTHER INFORMATION: Synthetic Construct (RFT1)

<400> SEQUENCE: 9
ctaggaagag tcggacggag ctg                                        23

<210> SEQ ID NO 10
<211> LENGTH: 98
<212> TYPE: DNA
<213> ORGANISM: Artificial Sequecne
<220> FEATURE:
<223> OTHER INFORMATION: Synthetic Construct (RFL1)
<220> FEATURE:
<221> NAME/KEY: misc_feature
<222> LOCATION: (17)..(86)
<223> OTHER INFORMATION: n is a, c, g, or t

<400> SEQUENCE: 10
cacggatcct gacaagnnnn nnnnnnnnnn nnnnnnnnnn nnnnnnnnnn nnnnnnnnnn   60
nnnnnnnnnn nnnnnnnnnn nnnnnncagc tccgtccg                          98

<210> SEQ ID NO 11
<211> LENGTH: 98
<212> TYPE: DNA
<213> ORGANISM: Artificial Sequence
<220> FEATURE:
<223> OTHER INFORMATION: Synthetic Construct (RFSS1)

<400> SEQUENCE: 11
cacgctgtac ggatgagtcg cgagcctgcg accggaaatg aaagatcttt cgcgttttgc   60
tcatgcgatg gatttttac agtgggcagc tccgtccg                           98

<210> SEQ ID NO 12
<211> LENGTH: 70
<212> TYPE: DNA
<213> ORGANISM: Artificial Sequence
<220> FEATURE:
<223> OTHER INFORMATION: Synthetic Construct (EC1TM)

<400> SEQUENCE: 12
gatgtgcgtt gagctcacct gcgaccggaa cactactgac actggggatg gatttcttta   60
cagttgtgtg                                                         70

<210> SEQ ID NO 13
<211> LENGTH: 50
<212> TYPE: DNA
<213> ORGANISM: Artificial Sequence
<220> FEATURE:
<223> OTHER INFORMATION: Synthetic Construct (LM-RFDT)

<400> SEQUENCE: 13
ctttgcataa ttcatggact acgtacgttg aaaagggagg ctatactagg             50
```

<210> SEQ ID NO 14
<211> LENGTH: 22
<212> TYPE: DNA
<213> ORGANISM: Artificial Sequence
<220> FEATURE:
<223> OTHER INFORMATION: Synthetic Construct (ST-RFDT)

<400> SEQUENCE: 14
ttattgattg cccccggcta gg                                          22

<210> SEQ ID NO 15
<211> LENGTH: 127
<212> TYPE: DNA
<213> ORGANISM: Artificial Sequence
<220> FEATURE:
<223> OTHER INFORMATION: Synthetic Construct (RFD-EC1)
<220> FEATURE:
<221> NAME/KEY: misc_feature
<222> LOCATION: (112)..(112)
<223> OTHER INFORMATION: n=fluorescein-dT
<220> FEATURE:
<221> NAME/KEY: misc_feature
<222> LOCATION: (113)..(113)
<223> OTHER INFORMATION: n=riboadenosine
<220> FEATURE:
<221> NAME/KEY: misc_feature
<222> LOCATION: (114)..(114)
<223> OTHER INFORMATION: n=dabcyl-dT

<400> SEQUENCE: 15
cacggatcct gacaaggatg tgtgcgttgt cgagacctgc gaccggaaca ctacactgtg    60
tgggatggat ttctttacag ttgtgtgcag ctccgtccga ctcttcctag cnnnggttcg   120
atcaaga                                                            127

<210> SEQ ID NO 16
<211> LENGTH: 14
<212> TYPE: DNA
<213> ORGANISM: Artificial Sequence
<220> FEATURE:
<223> OTHER INFORMATION: Synthetic Construct (FS1P1)
<220> FEATURE:
<221> NAME/KEY: misc_feature
<222> LOCATION: (13)..(13)
<223> OTHER INFORMATION: n=fluorescein-dT
<220> FEATURE:
<221> NAME/KEY: misc_feature
<222> LOCATION: (14)..(14)
<223> OTHER INFORMATION: n=dabcyl-dT

<400> SEQUENCE: 16
actcttccta gcnn                                                    14

<210> SEQ ID NO 17
<211> LENGTH: 14
<212> TYPE: DNA
<213> ORGANISM: Artificial Sequence
<220> FEATURE:
<223> OTHER INFORMATION: Synthetic Construct (FS1P2)
<220> FEATURE:
<221> NAME/KEY: misc_feature
<222> LOCATION: (1)..(1)
<223> OTHER INFORMATION: n=dabcyl-dT

<400> SEQUENCE: 17
nggttcgatc aaga                                                    14

CATALYTIC NUCLEIC ACID PROBES AS MICROBIAL INDICATORS

RELATED APPLICATIONS

This application is a national phase entry of PCT/CA2012/000205, filed Mar. 8, 2012, from U.S. Provisional patent application Ser. No. 61/450,169, filed on Mar. 8, 2011, the contents of each of these applications being incorporated herein by reference in their entirety.

INCORPORATION OF SEQUENCE LISTING

A computer readable form of the Sequence Listing "3244-P41273US00_SequenceListing.txt" (8,192 bytes), submitted via EFS-WEB and created on Sep. 6, 2013, is herein incorporated by reference.

Please replace the Sequence Listing currently of record with the Sequence Listing provided herewith in text format in computer readable form only.

FIELD

The application discloses a method of generating catalytic nucleic acid probes useful for detecting microorganisms such as bacterial pathogens. The application also discloses catalytic nucleic acid probes and methods of using the probes for detecting microorganisms.

BACKGROUND

Prevalence of food-borne pathogens, emergence of drug-resistant bacteria and viruses, and threat of bioterrorism are pressing concerns. Early detection of pathogens prevents outbreaks.

Traditionally, microbial detection is performed using microbiological techniques[1]. Although this approach is highly accurate, it can take days (even weeks) to arrive at a definitive conclusion. Both antibody and PCR based methods represent significant advances because such tests offer high specificity and sensitivity and require significantly reduced detection times[2]. However, these methods usually require multiple analytical steps and specialized equipment. There is a significant need for both simple methods that can achieve rapid detection of known pathogens and new platforms that can be quickly put in place to create assays for a new pathogen in an unanticipated outbreak.

DNAzymes, a special class of functional nucleic acids[3], are artificial single-stranded DNA molecules with a catalytic ability[4]. They can be isolated from a random-sequence DNA pool by the technique of "in vitro selection"[5] and have been explored as unique molecular tools for an increasing number of applications[4,6].

SUMMARY OF THE DISCLOSURE

The present disclosure describes a novel approach for bacterial pathogen detection by isolating fluorogenic DNAzymes from a random-sequence DNA library by in vitro selection using the unpurified complex extracellular mixture left behind by a specific microbe. Since both probe isolation and subsequent assaying procedures bypass tedious and time-consuming target identification steps, this method can be easily implemented for any microorganism.

The disclosure relates to a method of generating a catalytic nucleic acid probe for detecting a microorganism, the method comprising:

(a) contacting a plurality of candidate nucleic acid molecules with a microorganism target, wherein each of the candidate nucleic acid molecules comprises a variable region of nucleic acid sequence and a constant region of nucleic acid sequence comprising a detectable substrate, wherein the detectable substrate is detectable only upon cleavage of the detectable substrate, and (b) detecting the candidate nucleic acid molecule which (i) interacts with the microorganism target and (ii) has catalytic activity to cleave the detectable substrate upon interaction with the target, thereby generating a detectable signal, wherein the detected candidate nucleic acid molecule is a catalytic nucleic acid probe.

In one embodiment, the method also includes contacting the plurality of candidate nucleic acid molecules with a negative control target prior to contacting the plurality of candidate nucleic acids with the microorganism target and detecting a candidate nucleic acid which (i) interacts with the microorganism target, (ii) has catalytic activity to cleave the detectable substrate upon interaction with the target, thereby generating a detectable signal and (iii) does not cleave the detectable substrate upon interaction with the negative control target.

Optionally, the method further comprises:

(A) selecting a plurality of candidate nucleic acid molecules which (i) interact with the microorganism target and (ii) have catalytic activity to cleave the detectable substrate upon interaction with the target, thereby generating a detectable signal, wherein the plurality of candidate nucleic acid molecules constitute a pool of candidate nucleic acid molecules, (B) amplifying the variable region of nucleic acid sequence of each of the candidate nucleic acid molecules in the pool of candidate nucleic acid molecules, (C) ligating each of the amplified regions to the constant region of nucleic acid sequence, (D) contacting the ligated molecules with the microorganism target, and (E) selecting a further plurality of candidate nucleic acid molecules which (i) interact with the microorganism target and (ii) have catalytic activity to cleave the detectable substrate upon interaction with the target, thereby generating a detectable signal, wherein the further plurality of candidate nucleic acid molecules constitute an enriched pool of candidate nucleic acid molecules.

In one embodiment, the method comprises multiple cycles of steps (A) through (E), optionally at least 5, 15, 20, or 30 cycles of steps (A) though (E). In another embodiment, the pool of candidate nucleic acid molecules becomes increasingly enriched for candidate nucleic acid molecules which (i) interact with the microorganism target and (ii) have catalytic activity to cleave the detectable substrate upon interaction with the target, thereby generating a detectable signal, upon each successive cycle. An "enriched pool" refers to a pool of molecules that has a greater proportion of candidate nucleic acid molecules compared to non-candidate nucleic acid molecules than a comparator pool. Optionally, non-candidate nucleic acid molecules are molecules that do not (i) interact with the microorganism target and (ii) have catalytic activity to cleave the detectable substrate upon interaction with the target, thereby generating a detectable signal. Other non-candidate nucleic acid molecules include molecules that cleave the substrate non-specifically (for example, in the presence of a negative control target) or generate a detectable signal non-specifically.

In one embodiment, DNA is extracted from the enriched pool corresponding to the final, or last, cycle and a nucleic acid corresponding to catalytic nucleic acid probe is sequenced and/or cloned.

In one embodiment of the present method, the catalytic nucleic acid probe is a DNAzyme. Optionally, the DNAzyme catalyses the cleavage of a RNA-DNA linkage.

In another embodiment, the detectable substrate is a single ribonucleotide linkage embedded in a DNA sequence. In another embodiment, the ribonucleotide is flanked by a fluorophore modified nucleic acid residue on one side and a quencher modified nucleic acid residue on the other side and the fluorophore is quenched until the ribonucleotide linkage is cleaved, thereby generating a fluorogenic signal.

In one embodiment of the method, the microorganism target is found in the extracellular matrix of the microorganism. Optionally, the microorganism target is found in the intracellular matrix of the microorganism.

In another embodiment, the target is a protein, a DNA molecule, a RNA molecule, a small molecule, extracellular matrix, intracellular matrix, a cell of the microorganism, or any combination thereof. Optionally, the target is crude extracellular matrix or crude intracellular matrix.

Optionally, the microorganism is a bacteria, optionally a bacterial pathogen. In one embodiment, the microorganism is *E. coli, L. monocytogenes* or *S. typhimurium*.

In yet another embodiment, the method further comprises the use of the catalytic nucleic acid probe for detecting the microorganism.

The disclosure also relates to a catalytic nucleic acid probe for detecting a microorganism, wherein the catalytic nucleic acid probe comprises a first nucleic acid region that (i) interacts with a microorganism target and (ii) has catalytic activity to cleave a detectable substrate upon interaction with the target, thereby generating a detectable signal.

Optionally, the catalytic nucleic acid probe further comprises a second nucleic acid region comprising the detectable substrate.

In one embodiment, the detectable substrate is a single ribonucleotide linkage embedded in a DNA sequence and the ribonucleotide is flanked by a fluorophore modified nucleic acid residue on one side and a quencher modified nucleic acid residue on the other side such that the fluorophore is quenched until the ribonucleotide linkage is cleaved, thereby generating a fluorogenic signal.

In another embodiment, the catalytic nucleic acid probe comprises a sequence with at least 80%, 90%, 95% or 99% sequence identity to any one of SEQ ID NO: 1, SEQ ID NO: 2, SEQ ID NO: 3, SEQ ID NO: 4 or SEQ ID NO: 15. Optionally, the catalytic nucleic acid probe comprises, or consists essentially of, SEQ ID NO: 1, SEQ ID NO: 2, SEQ ID NO: 3, SEQ ID NO: 4 or residues 1-99 of SEQ ID NO: 15.

In yet another embodiment, the catalytic nucleic acid probe comprises a sequence with at least 80%, 90%, 95% or 99% sequence identity to SEQ ID NO: 5. Optionally, the catalytic nucleic acid probe comprises, or consists essentially of, SEQ ID NO: 5.

In another embodiment of the disclosure, the catalytic nucleic acid probe comprises (a) a sequence with at least 80%, 90%, 95% or 99% sequence identity to any one of SEQ ID NO: 1, SEQ ID NO: 2, SEQ ID NO: 3, SEQ ID NO: 4 or residues 1-99 of SEQ ID NO: 15 and (b) a sequence with at least 80%, 90%, 95% or 99% sequence identity to SEQ ID NO: 5.

In other embodiments, the catalytic nucleic acid probe is a DNAzyme.

The disclosure also relates to a kit for detecting a microorganism, wherein the kit comprises:
(1) a first catalytic nucleic acid that (i) interacts with a microorganism target and (ii) has catalytic activity to cleave a detectable substrate upon interaction with the target,
(2) a second nucleic acid comprising the detectable substrate of the first catalytic nucleic acid wherein a detectable signal is generated upon cleavage of the detectable substrate, and
(3) instructions for the use of the kit to detect a microorganism.

Optionally, the detectable substrate is a single ribonucleotide linkage embedded in a DNA sequence. In another embodiment, the ribonucleotide is flanked by a fluorophore modified nucleic acid residue on one side and a quencher modified nucleic acid residue on the other side such that the fluorophore is quenched until the ribonucleotide linkage is cleaved, thereby generating a fluorogenic signal.

In other embodiments, the first catalytic nucleic acid comprises a sequence with at least 80%, 90%, 95% or 99% sequence identity to any one of SEQ ID NO: 1, SEQ ID NO: 2, SEQ ID NO: 3, SEQ ID NO: 4 or residues 1-99 of SEQ ID NO: 15. Optionally, the second nucleic acid comprises a sequence with at least 80%, 90%, 95% or 99% sequence identity to SEQ ID NO: 5.

In a further embodiment, the first catalytic nucleic acid and the second nucleic acid comprise a single nucleic acid probe. Optionally, the nucleic acid probe is a DNAzyme.

The disclosure also relates to a method of detecting a microorganism in a sample comprising:
exposing the sample to a catalytic nucleic acid probe, wherein the catalytic nucleic acid probe (i) interacts with a microorganism target and (ii) cleaves a detectable substrate upon interaction of the catalytic nucleic acid probe with the target thereby generating a signal that indicates the presence of the microorganism in the sample.

In one embodiment, the detectable substrate is a single ribonucleotide linkage embedded in a DNA sequence. In another embodiment, the ribonucleotide is flanked by a fluorophore modified nucleic acid residue on one side and a quencher modified nucleic acid residue on the other side such that the fluorophore is quenched until the ribonucleotide linkage is cleaved, thereby generating a fluorogenic signal.

In one embodiment of the method, a single colony forming unit of the microorganism is detected. Optionally, at least 2, 3, 5, 10 or 20 colony forming units of the microorganism are detected.

In yet another embodiment, the microorganism is a bacterial pathogen, optionally selected from the group consisting of *E. coli, L. monocytogenes* and *S. typhimurium*.

In another embodiment, the target is a protein, a DNA molecule, a RNA molecule, a small molecule, extracellular matrix, intracellular matrix, a cell of the microorganism, or any combination thereof. Optionally, the target is crude extracellular matrix or crude intracellular matrix.

The disclosure also relates to the use of a catalytic nucleic acid probe for detecting a microorganism in a sample wherein the catalytic nucleic acid probe (i) interacts with a microorganism target and (ii) cleaves a detectable substrate upon interaction of the catalytic nucleic acid probe with the target thereby generating a signal that indicates the presence of the microorganism in the sample.

Optionally, the detectable substrate is a single ribonucleotide linkage embedded in a DNA sequence. In another embodiment, the ribonucleotide is flanked by a fluorophore modified nucleic acid residue on one side and a quencher modified nucleic acid residue on the other side such that the fluorophore is quenched until the ribonucleotide linkage is cleaved, thereby generating a fluorogenic signal.

In one embodiment, the microorganism is a bacterial pathogen, optionally selected from the group consisting of *E. coli, L. monocytogenes* and *S. typhimurium*.

In another embodiment, the target is a protein, a DNA molecule, a RNA molecule, a small molecule, extracellular matrix, intracellular matrix, a cell of the microorganism, or any combination thereof. Optionally, the target is crude extracellular matrix or crude intracellular matrix.

BRIEF DESCRIPTION OF THE DRAWINGS

Embodiments of the disclosure will be shown in relation to the drawings in which the following is shown.

RFL1 (SEQ ID NO: 10): DNA library with 70 random nucleotides (N70); FS1: fluorogenic substrate (SEQ ID NO: 5); FP1 (SEQ ID NO: 6): forward PCR primer; RP1 (SEQ ID NO: 7) and RP2 (SEQ ID NO: 8): two reverse PCR primers; RFT1 (SEQ ID NO: 9): the template for ligating FS1 to RFL1.

Figure 2:
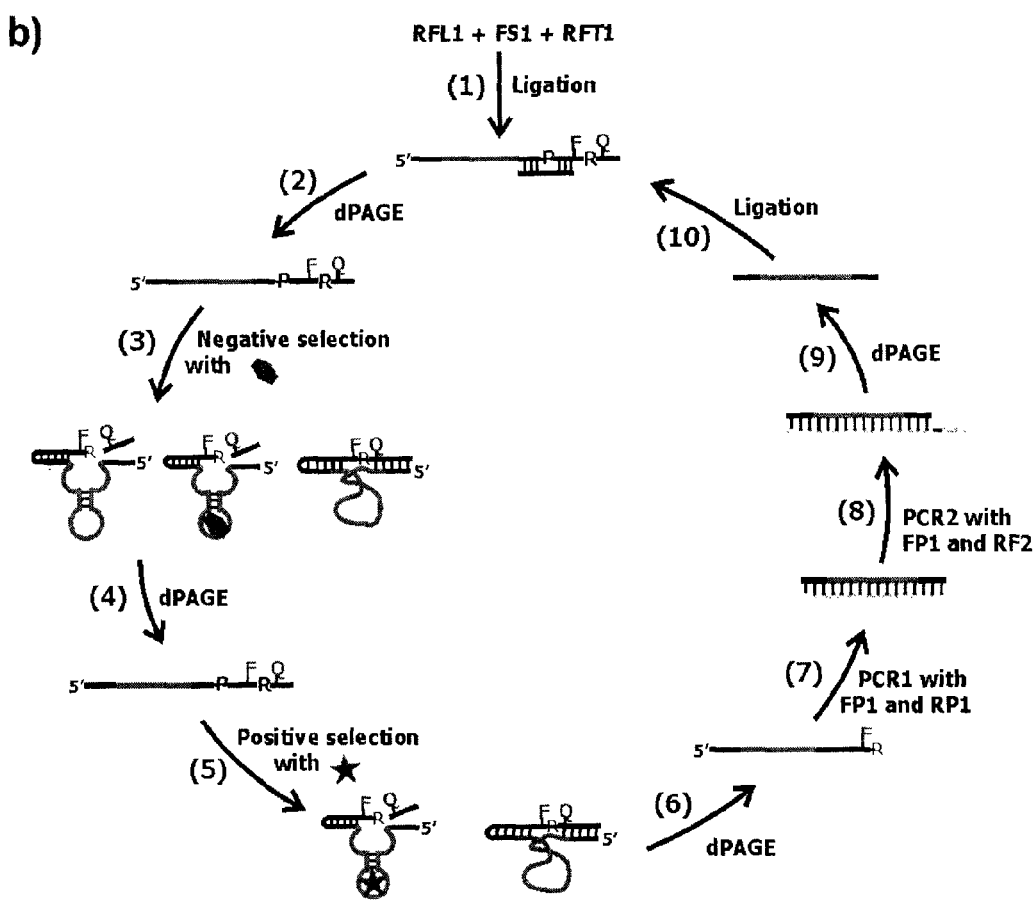
FIG. 2A shows the sequences of the DNA molecules used for the in vitro selection experiment.

FIG. 2B shows the in vitro selection scheme: (1) Ligation of FS1 to RFL1; (2) purification of ligated FS1-RFL1; (3) negative selection with CEM-BS; (4) purification of uncleaved FS1-RFL1 by dPAGE; (5) positive selection with CEM-EC; (6) purification of cleaved products by dPAGE; (7) PCR using FP1 and RP1 as primers; (8) PCR with FP1 and RP2 as primers (note: RP2 contains hexaethyleneglycol spacer and A20 tail at the 5' end—the hexaethyleneglycol spacer prevents the poly-A tail from being amplified, making the non-DNAzyme-coding strand 20 nucleotides longer than the coding strand); (9) purification of DNAzyme-coding strand by dPAGE; (10) ligation of RFL1 to FS1. The cycle of steps 2-10 was repeated for 19 times in this study.

FIG. 3 shows (A) the sequences of RFD-EC1 (SEQ ID NO: 15), the dominant DNAzyme obtained from in vitro selection, and RFSS1 (SEQ ID NO: 11) (a control), (B) signaling profiles of 100 nM RFD-EC1 or RFSS1 in the presence of CEM-EC. CEM-EC was incubated in SB alone for 5 min, followed by the addition of RFD-EC1 or RFSS1 and further incubation for 55 min and (C) PAGE analysis of the cleavage reaction mixtures of RFDEC1 and RFSS1.

Figure 4:
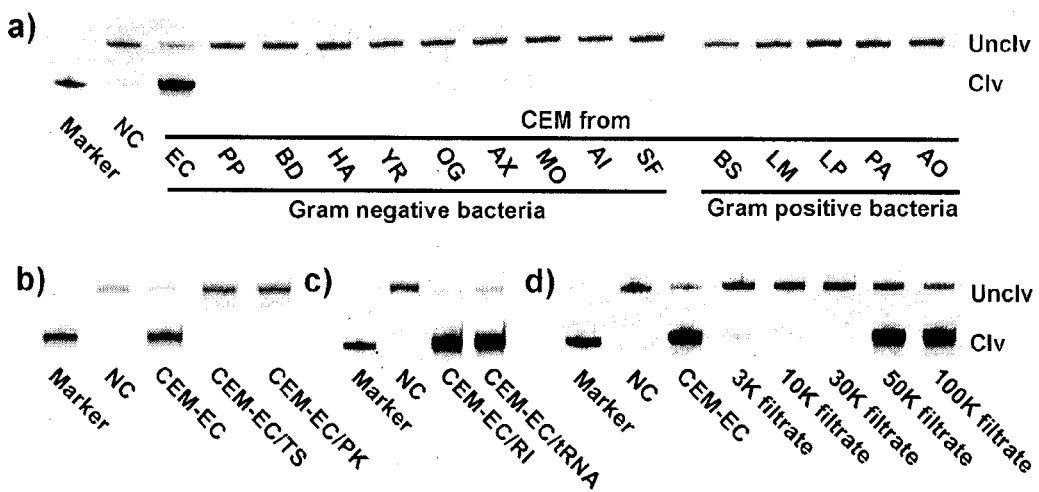

FIG. 4 shows (A) the response of RFD-EC1 to the CEM from various gram-negative and gram-positive bacteria. The gram-negative bacteria used were *Pseudomonas peli* (PP), *Brevundimonas diminuta* (BD), *Hafnia alvei* (HA), *Yersinia ruckeri* (YR), *Ochrobactrum grignonese* (OG), *Achromobacter xylosoxidans* (AX), *Moraxella osloensis* (MO), *Acinetobacter lwoffi* (AI), and *Serratia fonticola* (SF). The gram-positive bacteria used were *Bacillus subtilis* (BS), *Leuconostoc mesenteroides* (LM), *Lactobacillus plantarum* (LP), *Pediococcus acidilactici* (PA), and *Actinomyces orientalis* (AO). (B) Response of RFDEC1 to CEM-EC pre-treated with two proteases, trypsin (TS) and proteinase K (PK). (C) Response of RFD-EC1 to CEM-EC containing Ribolock (RI, an RNase inhibitor) or 100-fold excess tRNA. (D) Experiment to estimate the molecular weight of the potential protein target that triggers RFD-EC1. The reaction time for all the cleavage reactions was 1 h.

Figure 5:
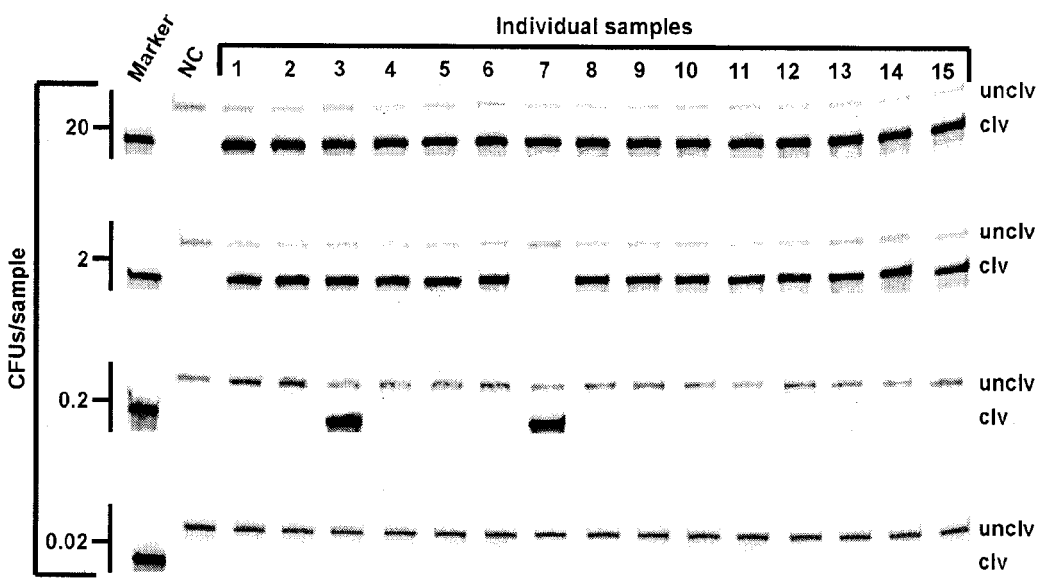

FIG. 5 shows single live cell detection. Shown in each row is the image of a dPAGE gel conducted to analyze 15 parallel cleavage reactions where RFD-EC1 was incubated with CEM-EC prepared from an overnight culture inoculated with 20 (top row), 2 (second row), 0.2 (third row) and 0.02 (bottom row) colony forming units (CFUs) of *E. coli*.

Figure 6:
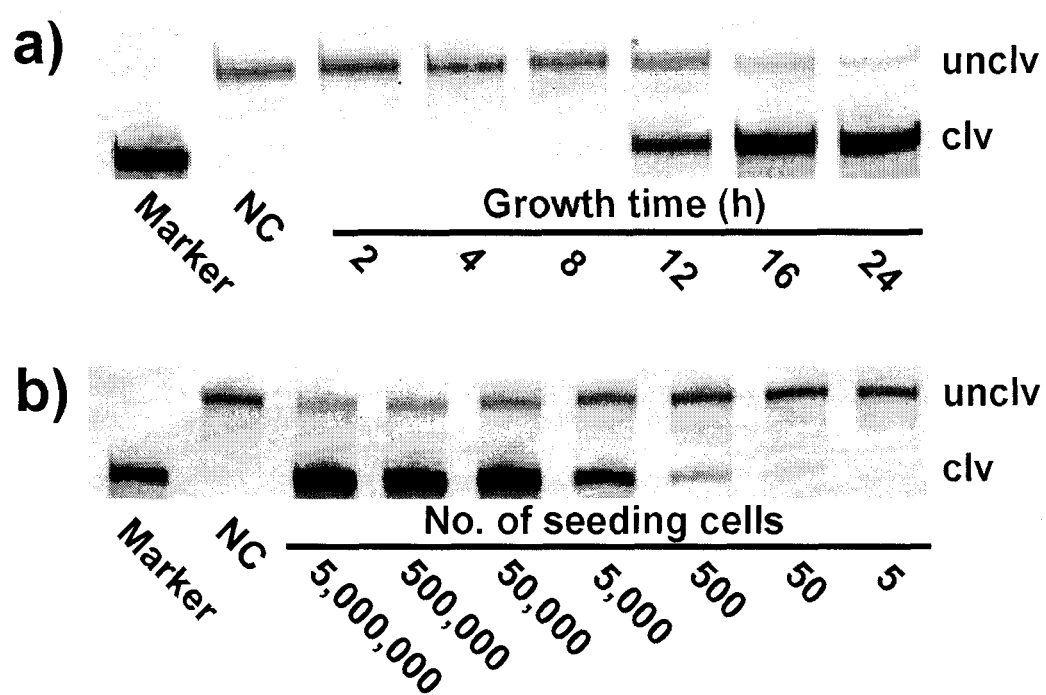

FIG. 6 shows (A) the growth time required for achieving single cell detection and (B) the detection limit of the assay when cells were cultured for 6 h.

Figure 7:
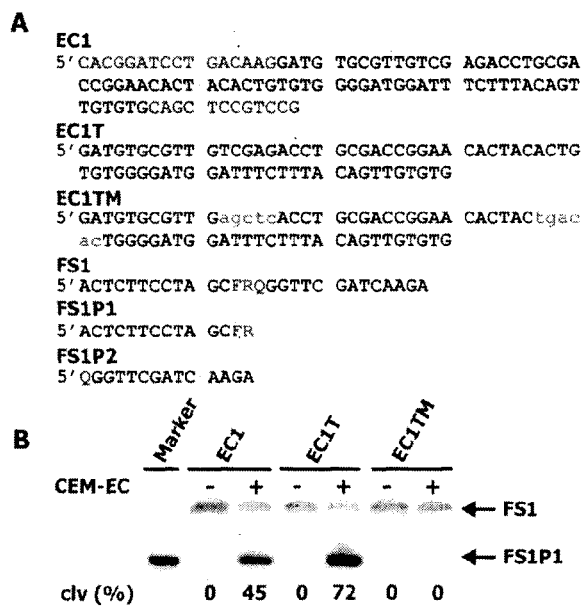

FIG. 7 shows that the DNAzyme functions in trans (the DNAzyme and the substrate exist separately). A) The oligonucleotide sequences: EC1 (SEQ ID NO: 1) is a full length DNAzyme including primer binding sites (red) previously obtained from in vitro selection, EC1T (SEQ ID NO: 2) is the truncated version of EC1 after removing the primer binding sites, EC1TM (SEQ ID NO: 12) is the mutated version of EC1T (mutated nucleotides are shown as small case letters in grey) and FS1 (SEQ ID NO: 5) is the full-length substrate composed of riboadenosine (blue R) flanked by a fluorophore modified deoxythymidine (fluorescein-dT; green F) and a quencher modified deoxythymidine (dabcyl-dT; red Q). FS1P1 (SEQ ID NO: 16) and FS1P2 (SEQ ID NO: 17) represent the 5'- and 3'-cleavage products of FS1 respectively. B) Fluorescent image of 10% dPAGE of the cleavage reaction mixtures of EC1, EC1T and EC1TM with FS1 in the absence (−) and presence (+) of *E. coli* CEM (CEM-EC). The percentage of cleavage (clv %) by the respective sequence was calculated using previously reported methods. The marker, FS1P1, was prepared by treating FS1 with 0.25M NaOH at 90° C. for 10 min.

Figure 8:
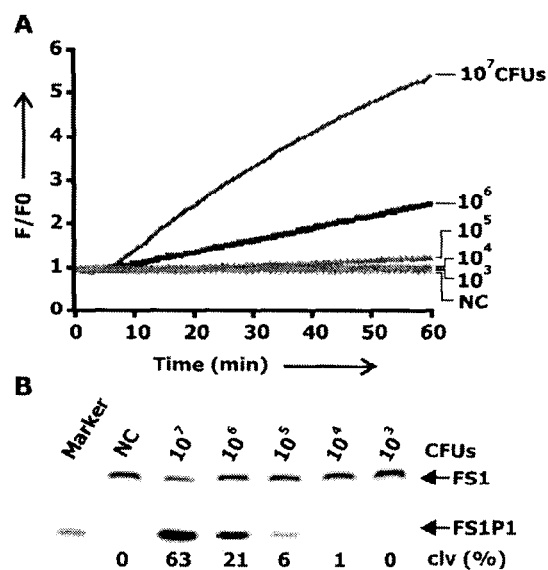

FIG. 8 shows a sensitivity test of EC1T in trans-acting form with varying number of *E. coli* cells. A) Real time fluorescence signalling profile in the presence of crude intracellular matrices (CIMs) collected from different number of *E. coli* cells as indicated. B) Fluorescent gel image of the samples used for fluorescent signal generation in (A).

Figure 9:
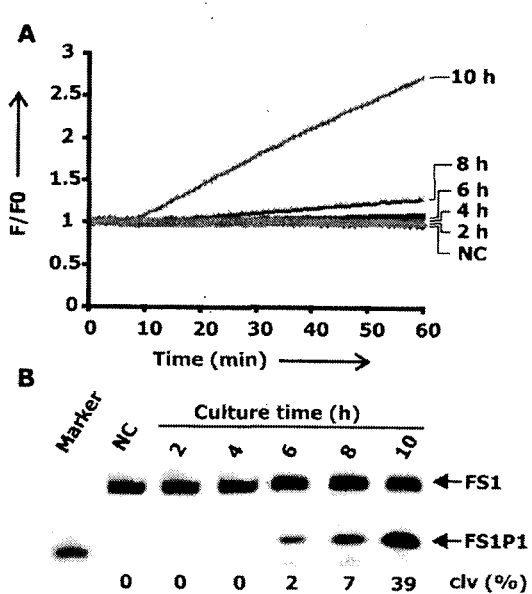

FIG. 9 shows the culturing time required to detect a single live *E. coli* bacterium (1 CFU) with trans-acting EC1T. A) Monitoring fluorescence signal generation in real time in the presence of the CIMs collected from a single cell culture at different time points as shown in the figure. B) dPAGE analysis of the reaction mixtures of (A).

Figure 10:
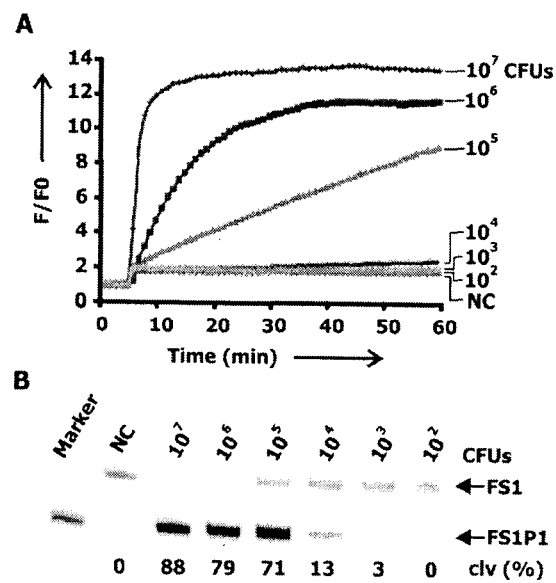

FIG. 10 shows a sensitivity test of cis-acting EC1 with varying number of EC cells. A) Real time fluorescence signalling profile in the presence of CIMs collected from different number of *E. coli* cells as indicated. B) Fluorescent gel image of the samples used for fluorescent signal generation in (A).

Figure 11:
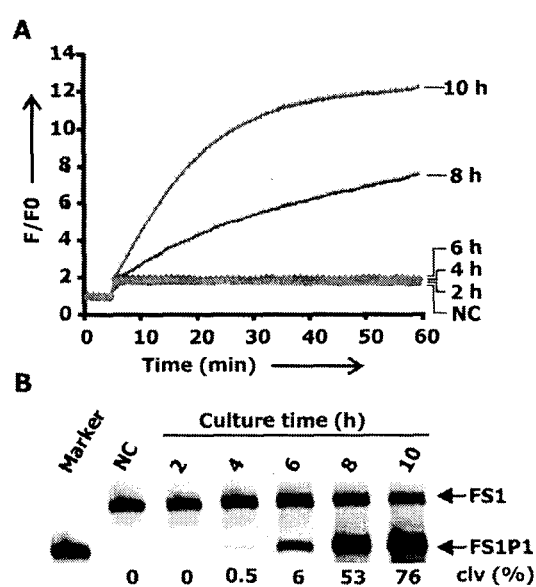

FIG. 11 shows the culturing time required to detect a single live *E. coli* bacterium (1 CFU) with cis-acting EC1. A) Monitoring fluorescence signal generation in real time in the presence of the CIMs collected from a single cell culture at different time points as shown in the figure. B) dPAGE analysis of the reaction mixtures of (A).

FIG. 12A shows the response of EC1T to *E. coli* crude extracellular mixture (CEM) and crude intracellular mixture (CIM). NC is a negative control where the reaction was conducted in SB alone excluding CEM and CIM. The image was obtained by a fluorescent scanner. FIG. 12B shows the fluorescent gel image of the reaction mixtures of EC1T with FS1 in presence of CIMs collected from *E. coli* cells after culturing in various culture broths: Luria-Bertani medium (LB), lysogeny broth miller (LBM), super optimal broth (SOB), super optimal broth with glucose (catabolite repression; SOC), tryptone broth (TB), Todd-Hewitt broth (THB), tryptic soy broth (TSB).

FIG. 13A shows the effect of divalent metal ions (Ba, Cd, Co, Mg, Mn, Ni, Cu, Zn and Ca) in the cleavage reaction of EC1T. NC is a negative control where the reaction was conducted in the SB alone. FIG. 13A shows the effect of Ba ion concentration as indicated above each lane in the reaction mixture of EC1T. Clv % for each sample was calculated following our previously reported method (ref, CJC).

FIG. 14 shows the cleavage activity of EC1T and CIM-EC under various reaction conditions. A) Cleavage percents (clv %) of each reaction condition in panels B, C and D, respectively, were calculated by subtracting clv % of the control condition (CC) and the test condition (TC). The CC was defined as the reaction condition (RC) with no CIM-EC. The inset gel in panel A is a representative dPAGE gel. B) Activity response of EC1T to CIM-EC when incubated at various temperatures (4, 15, 23, 37 and 50° C.); (*) reactions had non-target mediated cleavage diminishing the calculated clv % at the respective temperature. RC1=50 mM HEPES (pH 7.5); 150 mM NaCl and 15 mM $BaCl_2$. C) Activity response at different pH values. RC2=50 mM buffer agent (MES for pH 5.0-6:0; HEPES for pH 6.5-8.0; Tris-HCl for pH 8.5-9.0), 150 mM NaCl, and 15 mM $BaCl_2$. D) Cleavage activity at various substrate (FS1) to DNAzyme (EC1T) ratios.

FIG. 15 shows DNAzyme probes for *Listeria monocytogenes* (LM) and *Salmonella typhimurium* (ST) as well as their signaling properties. (A) LM-RFD (SEQ ID NO: 3) is a DNAzyme isolated for LM; LM-RFDT (SEQ ID NO:13) is a mutant version of LM-RFD (mutated nucleotides are shown as gray small letters); FS1 is the DNA-RNA chimeric substrate: F (green) is a fluorescein modified dT, R (blue) is a ribonucleotide, and Q refers a dabcyl modified dT. (B) Fluorescence signaling properties of LM-RFD and LM-RFDT in presence of crude intracellular mixture of LM (CIM-LM). NC is a negative control where the cleavage reaction was carried out in the reaction buffer while omitting CIM-LM. Insert is a fluorescent gel image of the corresponding cleavage reactions of fluorescence signal analysis. "Unclv": uncleaved FS1; "Clv": cleaved FS1. (C) ST-RFD (SEQ ID NO: 4) is a *Salmonella typhimurium* specific DNAzyme probe isolated by in vitro selection procedure. ST-RFDT (SEQ ID NO: 14) is a mutant version of ST-RFD (mutated nucleotides shown as gray small letters). FS1 (SEQ ID NO: 5) is the substrate which is exactly same as that for LM-RFD. D) Signaling properties of ST-RFD and ST-RFDT in the presence of crude extracellular mixture of ST (CIM-ST). Insert is a fluorescent gel image of the same samples used for signaling.

Figure 16:
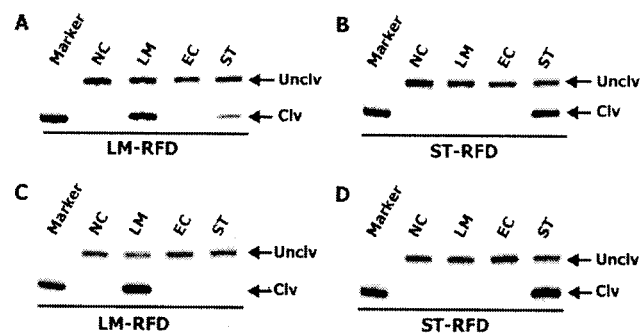

FIG. 16 show a specificity test of LM-RFD and ST-RFD with other pathogenic bacteria. (A) and (B) are the fluorescent images of dPAGE analysis of the cleavage reactions of LM-RFD and ST-RFD respectively with the CIMs obtained from *L. monocytogenes* (LM), *E. coli* O157:H7 (EC) and *S. typhimurium* (ST) grown in TSB (non-selective growth medium). NC is a negative control where the cleavage reaction was conducted with reaction buffer only. (C) and (D) represent the fluorescent image of dPAGE analysis of the cleavage reactions of LM-RFD and ST-RFD respectively with the CIMs obtained from LM, EC and ST gown in selective growth medium (UVM for LM and RVS for ST).

Figure 17:

FIG. 17 show a specificity test with different bacterial strains grown in selective culture media. (A) Fluorescent dPAGE image of the cleavage reactions of LM-RFD with the CIMs collected from various gram-negative and gram-positive bacteria grown in UVM. The gram-negative bacteria used were *Salmonella typhimurium* (ST), *Escherichia coli* O157:H7 (EC), *Brevundimonas diminuta* (BD), *Ochrobactrum grignonese* (OG), *Moraxella osloensis* (MO), *Acinetobacter lwoffi* (AI), and *Serratia fonticola* (SF). The gram-positive bacteria used were *Listeria monocytogenes* (LM), *Bacillus subtilis* (BS), *Actinomyces orientalis* (AO) and *Pediococcus acidilactici* (PA). (B) Fluorescent dPAGE image of the cleavage reactions of ST-RFD with the CIMs obtained from the above mentioned bacteria grown in RVS.

Figure 18:
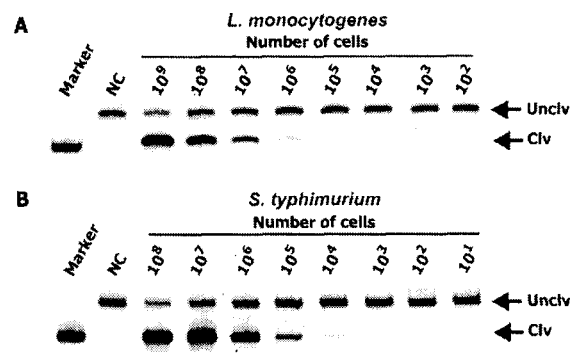

FIG. 18 shows a sensitivity test. Fluorescent gel images of the cleavage reactions of LM-RFD (A) and ST-RFD (B) with CIMs obtained from different number of LM and ST cells, respectively, as indicated above each lane. NC is a negative control where the reaction was carried out with the reaction buffer only.

Figure 19:
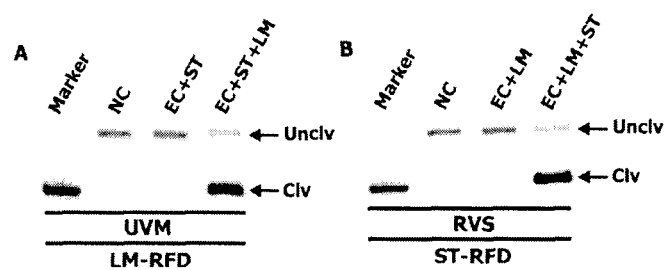

FIG. 19 shows the detection of specific bacteria from a mixed culture. (A) Fluorescent gel image of the cleavage reactions of LM-RFD with the CIMs collected from co-culture of EC+ST (as control) and EC+ST+LM. NC is a negative control wherein the cleavage reaction was carried out with the reaction buffer alone. (B) Fluorescent gel image of the cleavage reactions of ST-RFD with the CIMs collected from co-culture of EC+LM (as control) and EC+LM+ST.

Figure 20:
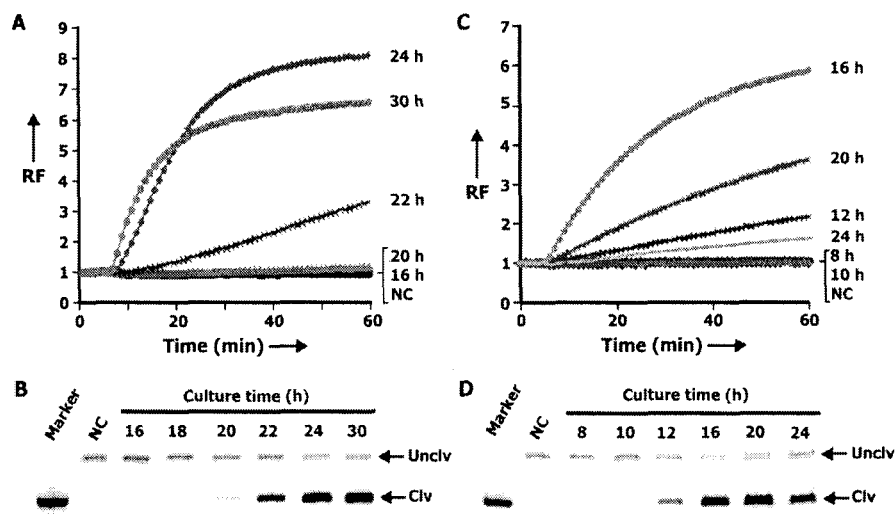

FIG. 20 shows the detection of a live single cell with food samples. (A) Fluorescent signal generation of LM-RFD with the samples of 1 CFU of LM grown in uvm with hot dog and collected at different time points as indicated in each graph line. NC is a negative control where the culture media was incubated with hot dog only without spiking with LM. (B) dPAGE analysis of the reaction mixtures obtained from the experiments in (A). (C) Fluorescence generation of ST-RFD with the samples of 1 CFU of ST grown in rvs with hot dog and collected at different time points as indicated in each graph line. NC is a negative control where the culture media was incubated with hot dog only without spiking with LM. (D) dPAGE analysis of the reaction mixtures obtained from the experiments in (C).

Figure 21:
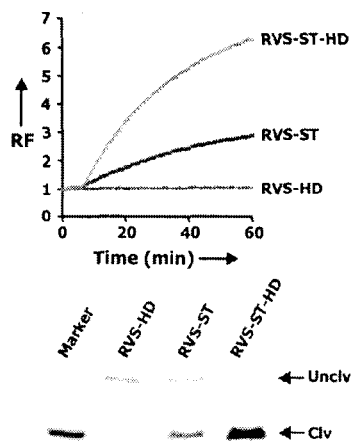

FIG. 21 shows the effect of hot dog in target excretion by ST in the growth medium. ST (1-2 CFU) was allowed to grown in RVS medium either in presence or absence of hot dog. In a control experiment only hot dog was incubated in RVS without spiking with ST. All were incubated at 37° C. for 20 h and the supernatants were collected from each culture tubes. These supernatants were passed through spin columns of 10 K molecular cut-off size and washed with 1×SB to remove malachite green in the RVS. The samples from the top of the filter membrane were collected to fresh tubes and used for cleavage reaction. The cleavage reactions with each samples as labeled in the figures were conducted in a fluorimeter for obtaining the real time fluorescence signal profile (A) and thereafter analyzed by a 10% dPAGE (B).

DETAILED DESCRIPTION

The present disclosure relates to methods for generating catalytic nucleic acid molecules for detecting microorganisms. The disclosure also provides catalytic nucleic acid molecules for detecting microorganisms and methods of using catalytic nucleic acid molecules for detecting microorganisms.

Accordingly, in one embodiment of the disclosure, there is included a method of generating a catalytic nucleic acid molecule for detecting a microorganism, the method comprising:

(a) contacting a plurality of candidate nucleic acid molecules with a microorganism target, wherein each of the candidate nucleic acid molecules comprises a variable region of nucleic acid sequence and a constant region of nucleic acid sequence comprising a detectable substrate, wherein the detectable substrate is detectable only upon cleavage of the detectable substrate, and (b) detecting a candidate nucleic acid molecule which (i) interacts with the microorganism target and (ii) has catalytic activity to cleave the detectable substrate upon interaction with the target, thereby generating a detectable signal, wherein the detected candidate nucleic acid molecule is a catalytic nucleic acid probe.

As used herein, the term "microorganism" refers to a microscopic organism that comprises either a single cell or a cluster of single cells. Microorganisms include, but are not limited to, bacteria, fungi, archaea, protists, algae, plankton and planarian. In one embodiment of the present disclosure, the microorganism is a gram-negative bacterium, for example *Escherichia coli* O157:H7, *Escherichia coli* K12, *Salmonella typhimurium, Pseudomonas peli, Brevundimonas diminuta, Hafnia alvei, Yersinia ruckeri, Ochrobactrum grignonese, Achromobacter xylosoxidans, Moraxella osloensis, Acinetobacter Iwoffi*, and *Serratia fonticola*. In another embodiment, the microorganism is a gram-positive bacterium, for example *Listeria monocytogenes, Bacillus subtilis, Actinomyces orientalis, Pediococcus acidilactici, Leuconostoc mesenteroides*, and *Lactobacillus planturum*. In specific embodiments of the invention, the microorganism is a pathogenic bacterium (for example, a bacterium that causes bacterial infection) such as *Escherichia coli* O157:H7, *Listeria monocytogenes, Salmonella typhimurium* or *Clostridium difficile*. In other embodiments, the microorganism is a harmless strain of bacteria.

As used in the present disclosure, "catalytic nucleic acid probes" and "catalytic nucleic acid molecules" are nucleic acid molecules that function as both binding agents and enzymes. The enzymatic activity of the catalytic nucleic acid probes of the present disclosure is activated upon interaction with a target. Catalytic nucleic acid probes are optionally DNA molecules (DNAzymes) or RNA molecules (ribozymes). In one embodiment of the present disclosure, the catalytic nucleic acid probe is a DNAzyme that cleaves a particular substrate, for example a ribonucleotide linkage.

The term "substrate" as used herein refers to a molecule that is modified, for example cleaved, by a catalytic nucleic acid probe at a cleavage site in the substrate, typically a cleavable linkage. For an RNA-cleaving DNAzyme, the substrate comprises a RNA-DNA linkage. Other substrates of catalytic nucleic acid probes include, but are not limited to, nucleic acids, modified nucleic acids, specific DNA or RNA sequences or a synthetic polymer containing a cleavable linkage such as an ester or amide. Optionally, a catalytic nucleic acid probe includes a substrate of the catalytic nucleic acid probe.

As used herein, a "detectable substrate" is a substrate where the cleavage of the substrate results in a signal that can be detected. The substrate is not detectable prior to cleavage, for example, because the signal is quenched. In one embodiment, a signal is generated or emitted when a detectable substrate is cleaved to activate a signal agent. Optionally, the signal is a fluorogenic signal, a colorimetic signal, an electrochemical signal, a surface plasmon resonance (SPR) signal or a radioactive signal.

In one embodiment of the present invention, a catalytic nucleic acid probe interacts with a microorganism target. As used herein, a "microorganism target" is a molecule, compound or substance that is present in or on the microorganism or is generated, excreted, secreted or metabolized by the microorganism. In one embodiment of the invention, a microorganism target is present in the extracellular matrix of the microorganism. In another embodiment, a microorganism target is present in the intracellular matrix of an organism. In another embodiment, a microorganism target comprises a protein, a DNA molecule, a RNA molecule, a small molecule, extracellular matrix, intracellular matrix, a cell of the microorganism, or any combination thereof. Optionally, a microorganism target is a crude or purified extracellular matrix or a crude or purified intracellular matrix. In other embodiments, a microorganism target is specific to a particular species or strain of microorganism.

As used herein, the term "interacts with a microorganism target" includes direct and indirect binding of a catalytic nucleic acid molecule to a target. In some embodiments, the binding is transitory, but sufficient to activate catalytic activity. The term "interacts with a microorganism target" is not limited to binding to a target but could include any other association between the catalytic nucleic acid molecules and the target sufficient to activate catalytic activity.

"Candidate nucleic acid molecules" are nucleic acid molecules that are screened against a microorganism target, in order to identify the catalytic nucleic acid probes of the present discourse. In one embodiment, a candidate nucleic acid molecule comprises a variable region of nucleic acid sequence and a constant region of nucleic acid sequence comprising a detectable substrate, wherein the detectable substrate is detectable only upon cleavage of the detectable substrate. As used herein, a "variable region" is a nucleic acid sequence that differs among the various candidate nucleic acid molecules. Optionally, the "variable region" comprises a random sequence of nucleic acid sequence. In one embodiment, each nucleic acid residue in the variable region has a 20-30%, optionally 25%, probability of being an A, C, G or T nucleotide. In contrast, the "constant region" of the candidate nucleic acid molecules is the same in each of the candidate nucleic acid molecules. The constant region of nucleic acid sequence is optionally a detectable substrate, for example an RNA-DNA linkage. Optionally, the RNA residue is flanked on one side by a nucleotide labeled with a fluorophore and a nucleotide labeled with a quencher on the other side.

The candidate nucleic acid molecules of the present disclosure are optionally generated from a DNA library, optionally a single stranded DNA library. In one embodiment, the DNA library is DNA library RFL1 (obtained from Yale University Keck Facilities or Integrated DNA Technologies (IDT). Optionally, the DNA library comprises single stranded DNA molecules comprising a central variable domain flanked by two non-variable regions. In one embodiment, the central variable domain is 10 to 500 nucleotides in length, optionally 20 to 250, optionally 50 to 100 nucleotides in length. The constant regions may be 5 to 50 nucleotides in length, optionally 10 to 20 nucleotides in length. DNA library RFL1 contains molecules consisting of 98 nucleic acid molecules distributed into a central random-sequence domain of 70 nucleotides and two non-variable regions of 16 nucleotides and 12 nucleotides at the 5' and 3' ends. Each random position in the central variable domain optionally represents a 20-30%, optionally 25%, probability of being an A, C, G or T nucleotide.

To generate candidate nucleic acid molecules, the nucleic acids molecules comprising the DNA library are optionally ligated to a detectable substrate. As described above, a "detectable substrate" is a substrate which may be modified by a catalytic nucleic acid. In one embodiment of the present disclosure, the detectable substrate is a ribonucleotide-DNA linkage. Optionally, the modification is cleavage. Modification of the detectable substrate by a catalytic nucleic acid generates a signal that is detectable (a "detectable signal"). A person skilled in the art would understand that there are numerous ways to detect the presence of cleaved molecules in the sample. Optionally, the signal is a fluorogenic signal, a colorimetric signal, an electrochemical signal, a surface plasmon resonance (SPR) signal or a radioactive signal. In some embodiments, the substrate will be linked to a suitable signalling system (such as gold nanoparticles, gold surfaces, and electrochemical-sensitive molecules). The cleavage of the substrate alters the chemical or physical behaviour of the signalling system (such as the aggregate state of gold nanoparticles, the surface plasmon of gold surfaces, and the conductivity of the electrochemically active molecules), resulting in a colorimetric, SPR or electrochemical signal.

Optionally, the ribonucleotide is flanked on one side by a nucleotide labelled with a fluorophore and on the other side by a nucleotide labelled with a quencher. Optionally, the fluorophore is fluorescein and the quencher is dabcyl. In one embodiment, cleavage of the ribonucleotide leads to the release of the nucleotide labelled with the quencher, thereby generating a fluorogenic signal.

In one embodiment of the present disclosure, the catalytic nucleic acid probes are isolated using an in vitro selection process. According to the methods of the present disclosure, a plurality of candidate nucleic acid molecules, which, as described above, comprise both a variable region of nucleic acid sequence (optionally derived from a DNA library) and a constant region of nucleic acid sequence comprising a detectable substrate, are contacted with a microorganism target. In other embodiments, at least 1000, 10,000, 100,000 or 1,000,000 candidate nucleic acid molecules are contacted with a microorganism target. Optionally, at least $10^{14}$-$10^{16}$ unique molecules are contacted with a microorganism target. Optionally, contacting the molecules with a microorganism target comprises incubating the molecules in medium containing the target. In other embodiments, contacting the molecules with a microorganism target comprises incubating the molecules in extracellular matrix or intracellular matrix derived from a microorganism. The extracellular or intracellular matrix is optionally crude or purified matrix. Extracellular matrix is, optionally obtained by removing cells grown in culture media, optionally Luria-Bertani media.

In another embodiment, the target comprises a protein, a DNA molecule, a RNA molecule, a small molecule, extracellular matrix, intracellular matrix, a cell of the microorganism, or any combination thereof. The molecules are optionally contacted with the target for at least 5, 10, 20, 30, 45 or 60 minutes. In other embodiments, the molecules are contacted with the target for 1 to 60 minutes, optionally 5 to 45 minutes, optionally 20 to 40 minutes.

In one embodiment of the present methods, the plurality of candidate nucleic acid molecules are first contacted with a negative control target prior to being contacted with the microorganism target. Optionally, the negative control target is extracellular matrix or intracellular matrix from a microorganism that is not the microorganism of interest. In other embodiments, the negative control target is a protein, a DNA molecule, a RNA molecule, a small molecule, extracellular matrix, intracellular matrix, a cell of the microorganism, or any combination thereof derived from a microorganism that is not the microorganism of interest. Only nucleic acid molecules that remain uncleaved after contact with the negative control target are then contacted with the microorganism target. Optionally, uncleaved DNA molecules are purified by polyacrylamide gel electrophoresis. One of the goals of this "negative selection" step is to remove any self-cleaving or non-specific catalytic nucleic acid molecules.

The method optionally includes selecting at least one catalytic nucleic acid molecule from the plurality of nucleic acid molecules which (i) interacts with the target and (ii) cleaves the detectable substrate upon interaction with the target, thereby generating a detectable signal. Optionally, the method also includes selecting at least one catalytic nucleic acid molecule that is not cleaved upon interaction with the negative control target. Optionally, the method also includes selecting at least one catalytic nucleic acid molecule that is not self-cleaving in the absence of the target.

In one embodiment, candidate nucleic acid molecules which are cleaved during exposure to the microorganism target are purified, optionally by dPAGE, and amplified by PCR (polymerase chain reaction). In one embodiment, the variable region of random sequence is amplified. The amplified sequences are then optionally ligated to a detectable substrate and again exposed to the microorganism target. Optionally, at least 5, 10, 15, 20 or 30 cycles of selection, amplification, ligation, contacting (exposure) and selection are performed. Each cycle of election, amplification, ligation, contacting (exposure) and selection generates an increasingly enriched pool of catalytic nucleic acid probes. As used herein, "an enriched pool" refers to a pool of molecules that has a greater proportion of candidate nucleic acid molecules compared to non-candidate nucleic acid molecules than a comparator pool. Optionally, an enriched pool has at least a 2, 5, 10, 50, 100, 200 or 500% greater proportion of candidate nucleic acid molecules compared to non-candidate nucleic acid molecules than a non-enriched comparator pool. Optionally, non-candidate nucleic acid molecules are molecules that cleave the substrate non-specifically or generate a detectable signal non-specifically.

In one embodiment, DNA is extracted from the enriched pool corresponding to the final, or last, cycle and a nucleic acid corresponding to catalytic nucleic acid probe is sequenced and/or cloned to obtain a catalytic nucleic acid probe for detecting a microorganism target.

The present disclosure also relates to catalytic nucleic acid probes, for example DNAzymes, for detecting a microorganism. The catalytic nucleic acid probes are optionally generated by the methods described herein.

The catalytic nucleic acid probes comprise the following functionalities: (a) recognition of a microorganism target and (b) catalysis of a substrate, for example an RNA-DNA linkage, such that a signal is generated, in the presence of the microorganism target. Optionally, the RNA linkage is present in the catalytic nucleic acid probe itself.

Thus in some embodiments, the catalytic nucleic acid probe (i) interacts with a microorganism target and (ii) cleaves a substrate upon interaction with the target. The cleavage of the substrate optionally generates a detectable signal. In some embodiments, the substrate is part of the catalytic DNA molecule such that the catalytic molecule comprises both (a) a first catalytic nucleic acid region that interacts with the target and (b) a second nucleic acid region comprising the substrate.

The first catalytic nucleic acid region that interacts with the target is optionally 5 to 500 base pairs in length, optionally 10 to 200 base pairs in length, optionally 20-120 base pairs in length, optionally 22 to 100 base pairs in length. In some embodiments, the first nucleic acid region comprises a sequence with at least 80%, 90%, 95% or 99% sequence identity to any one of SEQ ID NO: 1, SEQ ID NO: 2, SEQ ID NO: 3, SEQ ID NO: 4 or residues 1-99 of SEQ ID NO: 15. In other embodiments, the first nucleic acid region comprises a sequence with optionally at least 5, 10, 15, 20, 30, 40, 50, 60, 70, 80, 90 or 100 base pairs that are contiguous with sequences contained in any one of SEQ ID NO: 1, SEQ ID NO: 2, SEQ ID NO: 3, SEQ ID NO: 4 or residues 1-99 of SEQ ID NO: 15. In other embodiments, the first nucleic acid region comprises or consists of any one of SEQ ID NO: 1, SEQ ID NO: 2, SEQ ID NO: 3, SEQ ID NO: 4 or residues 1-99 of SEQ ID NO: 15. Optionally, the first nucleic acid region has catalytic activity such that it modifies a substrate upon interaction with the target.

The second nucleic acid region comprising the substrate is optionally 10 to 60 base pairs in length, optionally 20-40 base pairs in length. Optionally, the substrate is a ribonucleotide and the ribonucleotide is flanked by a fluorophore modified nucleic acid residue on one side and a quencher modified nucleic acid residue on the other side. In some embodiments, the second nucleic acid region comprises a sequence with at least 80%, 90%, 95% or 99% sequence identity to SEQ ID NO: 5. In other embodiments, the second nucleic acid region comprises or consists of SEQ ID NO: 5.

In other embodiments, the catalytic nucleic acid probe comprises a sequence that hybridizes under medium or high stringency conditions to any one of SEQ ID No: 1-5 or residues 1-99 of SEQ ID NO: 15 or the complement thereof. Medium or high stringency hybridization are well known to persons skilled in the art. Examples of hybridization conditions may be found in molecular biology reference texts such as *Molecular Cloning: A Laboratory Manual* by Sambrook and Russell (3$^{rd}$ Edition, Cold Spring Harbour Press, 2001). Optionally, high stringency conditions comprise the following: hybridization at 5× sodium chloride/sodium citrate (SCC)/5×Denhardt's solution/1.0% SDS at Tm −5° C. for 15 minutes based on the equation (Tm=81.5° C.−16.6 (Log 10 [Na+])+0.41(% G+C)−600/l) (or similar equation)), followed by a wash of 0.2×SSC/0.1% SDS at 60° C. It is understood, however, that equivalent stringencies may be achieved using alternative buffers, salts and temperatures.

In other embodiments, the second nucleic acid region is contained on a separate nucleic acid molecule from the first nucleic acid region. This arrangement is optionally referred to as "in trans". In an "in cis" arrangement, both the first and second nucleic acid regions are present in the same molecule.

The catalytic nucleic acid molecules of the present disclosure may be synthesized using oligonucleotide synthesis methods known in the art. The entire catalytic nucleic acids may be optionally synthesized as one molecule or the first and second nucleic acid regions may be synthesized separately and combined together, for example by ligation.

The present disclosure also relates to a method for using the catalytic nucleic acid probes for indicating the presence of a microorganism. The catalytic nucleic acid probes are optionally created through the use of the methods described herein.

The catalytic nucleic acid probes described in the present disclosure are useful for detecting microorganisms in a food sample (eg. meat, fish, vegetables, fruit, eggs, dairy products etc.), a medical sample (blood, saliva, tissue sample etc.), a water sample, an environmental sample or any other sample where it is desired to know of the presence or absence of a microorganism. Optionally, the catalytic nucleic acid probes of the present disclosure are useful for identifying bacterial pathogens, optionally food borne bacterial pathogens.

The catalytic nucleic acid probes optionally detect a single live cell. In other embodiments, the catalytic nucleic acid probes optionally detect at least 0.2, 2 or 20 colony forming units.

In one embodiment of the present methods, at least a single microbial cell is isolated from a sample. The cell is optionally cultured in appropriate medium. In one embodiment, if one colony forming unit (a single live cell) is used to initiate cell growth, a culturing time of at least 4, 8, 12 or 16 hours may be used.

In one embodiment, a crude extracellular mixture is obtained from the cells by removing the cells (for example by centrifugation) from the media. In another embodiment, a protein, a DNA molecule, a RNA molecule or a small molecule is isolated from the cultured microbial cells. In another embodiment, crude intracellular matrix is obtained from the cultured cells.

Optionally, a catalytic nucleic acid probe corresponding to a specific microorganism target is exposed to, and contacted with, the extracellular matrix, intracellular matrix, protein, a DNA molecule, a RNA molecule or small molecule. Optionally, the catalytic nucleic acid probe is exposed to the whole microbial cell. The extracellular matrix, intracellular matrix, protein, a DNA molecule, a RNA molecule, small molecule or microbial cell is typically present in an appropriate media. The catalytic nucleic acid probe corresponding to a specific microorganism is exposed to the extracellular matrix, intracellular matrix, protein, a DNA molecule, a RNA molecule, small molecule and/or microbial cell optionally for at least: 5, 10, 30, 60 or 120 minutes. dPAGE analysis is optionally used to assay for cleavage of the probes. Cleavage of the probe will make the probe detectable, and detection indicates the presence of the specific microorganism corresponding to the target of the catalytic nucleic acid probe in the original sample.

In another aspect, the present disclosure includes a kit for determining the presence of a microorganism, said kit comprising 1) a first catalytic nucleic acid that (i) interacts with a microorganism target and (ii) has catalytic activity to cleave a detectable substrate upon interaction with the target, and (2) a second nucleic acid comprising the detectable substrate of the first catalytic nucleic acid wherein a detectable signal is generated upon cleavage of the detectable substrate.

In another embodiment, the kits disclosed herein also include, without limitation, containers, instructions for use, reagents for DNAzyme activity and or bacterial culturing, and other agents commonly used in the processes described herein.

All publications, patent and patent applications are herein incorporated by reference in their entirety.

EXAMPLES

Embodiments of the disclosure will be illustrated in a non-limiting way by reference to the examples below.

Example 1

Generation of Fluorogenic DNA Probes

Figure 1:
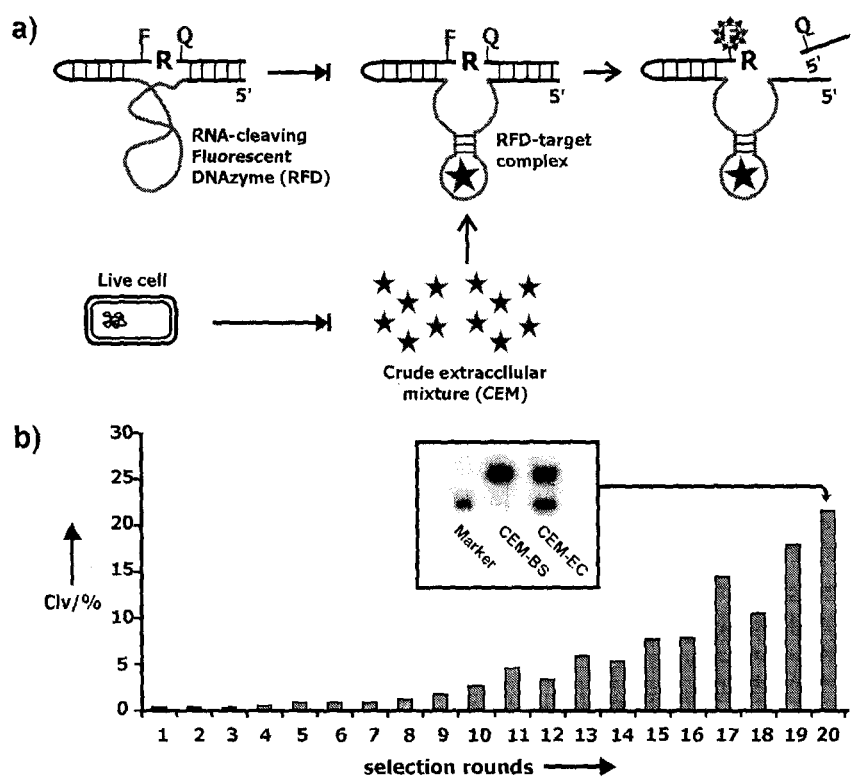
FIG. 1 shows (A) the conceptual design of fluorescent DNAzymes that fluoresce upon contact with the crude extracellular mixture (CEM) produced by live cells. F: fluorophore (specifically, fluorescein for this study); Q: quencher (dabcyl); R: ribonucleotide (ribo-A for this work). (B) In vitro selection progress. The DNAzyme selection progress was monitored through the percent cleavage of the DNA pool from each round of selection upon incubation with CEM-EC. The insert is the image of a dPAGE gel used to analyze the cleavage activity of the 20th DNA pool in the presence of CEM-BS and CEM-EC. The top band is the full-length DNA pool and bottom band is the cleaved product.

To demonstrate the feasibility of this method, fluorogenic DNA probes were generated based on an RNAcleaving fluorescent DNAzyme (RFD) system [7]. These DNAzymes cleave a lone RNA linkage (R; FIG. 1A) embedded in a DNA sequence and flanked by nucleotides labelled with a fluorophore (F; fluorescein-dT) and a quencher (Q; dabcyl-dT). These labels provide a convenient way to synchronize the catalysis of the DNAzyme with the generation of a fluorescence signal [7]. To date, several RFDs with distinct secondary structures, pH and metal ion dependences have been isolated [8]. Some of these DNAzymes have been explored for the design of fluorescent [9] or colorimetric [10] biosensing assays. In this study, RFDs that can respond directly to the CEM generated by the model microbe Escherichia coli (E. coli) were derived. E. coli is a Gram-negative bacterium commonly found in the lower intestine of warm-blooded organisms. Most E. coli strains are innocuous; some strains such as O157:H7, however, can cause deadly food poisoning in humans. In addition, E. coli is one of the best-studied microbes and holds a special status in microbiology and biotechnology. For this study, E. coli K12, a harmless strain commonly used in research laboratories was used. E. coli K12 is widely accessible by the research community, extremely safe to handle, and very easy to grow.

RFD Isolation Using the Random-Sequence DNA Library RFL1

The DNA library RFL1, the special fluorogenic substrate FS1, the forward PCR primer FP1, the two reverse PCR primers RP1 and RP2, RFT1, the template for ligating FS1 to RFL1 were purchased as synthetic oligonucleotides either from Yale University Keck Facilities or from Integrated DNA Technologies (IDT). Their sequences are provided in FIG. 2a. All oligonucleotides were purified by 10% denaturing polyacrylamide gel electrophoresis (dPAGE) before use. RFL1 contains 98 nucleotides (nt) distributed into a central random-sequence domain of 70 nt (N70 in light blue) and two constant regions of 16 nt and 12 nt at the 5' and 3' ends. Each random position represents a 25% probability of A, C, G or T nucleotides. The 28-nt FS1 contains an adenosine ribonucleotide (R in dark blue) as the cleavage site, flanked by a fluorescein-dT (F in green) and a dabcyl-dT (Q in red). The reverse primer RP2 contains hexaethyleneglycol spacer (L in grey) and A20 tail at the 5' end. The hexaethyleneglycol spacer prevents the poly-A tail from being amplified, making the non-DNAzyme-coding strand 20 nucleotides longer than the coding strand. This allows for the separation of the two strands by 10% dPAGE. The RNA-containing substrate FS1 was deprotected and purified by 10% dPAGE following the previously reported protocol.

The selection scheme is described as follows. Briefly, prior to the selection, two different CEM samples were prepared, one from E. coli, termed CEM-EC, and one from the control bacterium Bacillus subtilis (B. subtilis), termed CEM-BS; each CEM was prepared by removing cells grown overnight in Luria-Bertani media (LB; commonly used for culturing bacteria).

Specifically, E. coli K12 cells were grown overnight in 5 mL of LB with continuous shaking at 37° C. The cells were removed by centrifugation at 11,000 g for 5 min at room temperature. The crude supernatant was collected and aliquoted into microcentrifuge tubes and stored at −20° C. CEM-BS was prepared in an identical way as described for CEM-EC except that B. subtilis cells were grown. The CEM from other bacteria described herein were prepared in a similar way except that each bacterium was cultured in LB for a different period of time (because these bacteria have varying growth rates in LB) until the OD600 (optical density at 600 nm) of each cell culture reached ~1.

In Vitro Selection Procedure

The following steps are depicted in FIG. 2B.

Ligation of FS1 to RFL1 (step 1 in FIG. 2B)—200 pmol of FS1 was phosphorylated (reaction volume: 100 µL) with 10 µCi [γ-32P]ATP and 20 units of PNK for 15 min at 37° C. in 1×PNK buffer A (MBI Fermentas). This was followed by the addition of non-radioactive ATP to the final concentration of 1 mM and a further incubation at 37° C. for 20 min. The reaction was quenched by heating the mixture at 90° C. for 5 min. Equimolar RFL1 and RFT1 were then added to this solution and the mixture was heated at 90° C. for 40 s and cooled to room temperature for 10 min. Then, 20 µL of 10×T4 DNA ligase buffer (MBI Fermentas) was added and the volume was adjusted to 200 µL with ddH2O. This was followed by the addition of 20 units of T4 DNA ligase and incubation at room temperature for 1 h.

Purification of ligated FS1-RFL1 (step 2)—The DNA molecules in the mixture from step 1 were concentrated by ethanol precipitation and the ligated FS1-RFL1 molecules were purified by 10% dPAGE.

Negative selection (step 3)—The purified FS1-RFL1 was dissolved in 100 µL of 1× selection buffer (1×SB) (50 mM HEPES, pH 7.5, 150 mM NaCl, 15 mM MgCl2, and 0.01% Tween 20). This mixture was incubated at room temperature for 5 h. This was followed by the addition of 25 µL of CEM-BS as prepared above and 25 µL of 2×SB. The new mixture was further incubated at room temperature for 1 h. The reaction was quenched by the addition of 150 µL of stop solution containing 100 mM EDTA and 8 M urea.

Purification of uncleaved FS1-RFL1 (step 4)—After ethanol precipitation, the uncleaved FS1-RFL1 molecules from the above reaction mixture were purified by 10% dPAGE and stored at −20° C. until use.

Positive selection (step 5)—25 µL of CEM-EC was mixed with 25 µL of 2×SB and added to the uncleaved FS1-RFL1 obtained in step 4 above and the reaction volume was adjusted to 100 µL with 1×SB. The entire mixture was incubated at room temperature for 30 min before addition of 100 µL of stop solution.

Purification of cleaved products (step 6)—After ethanol precipitation, the large cleaved fragment (which contained RFL1 sequence) was purified by 10% dPAGE and used as the template for PCR in the next step. The percentage of cleaved RFL1 was also determined and used as a way to measure the progress of selection.

PCR1 (step 7)—The PCR mixture (50 µL) contained the template prepared above, 0.5 µM each of FP1 and RP1, 200 µM each of dNTPs (dATP, dCTP, dGTP and dTTP), 1×PCR buffer (75 mM Tris-HCl, pH 9.0, 2 mM MgCl2, 50 mM KCl, 20 mM (NH4)2SO4) and 2.5 units of Thermus thermophilus DNA polymerase. The DNA was amplified using the following thermocycling steps: 94° C. for 1 min; 13 cycles of 94° C. for 30 s, 50° C. for 45 s and 72° C. for 45 s; 72° C. for 1 min.

PCR2 (step 8)—1 µL of the above PCR1 product was diluted with ddH2O to 20 µL, 1 µL of which was used as the template for this additional PCR step using primers FP1 and RP2 while following the same protocol above for PCR1. Note that the numbers of amplification cycles between different selection rounds were adjusted, typically between 13 and 15 cycles, to achieve full amplification (revealed by 1% agarose gel electrophoresis).

Purification of DNAzyme-coding strand (step 9)—As stated above, the hexaethyleneglycol spacer in RP2 prevents the amplification of the A20 fragment, making the non-DNAzyme-coding strand 20 nucleotides longer than the coding strand. The coding strand RFL1 was purified by 10% PAGE in this step.

Ligation of RFL1 to FS1 (step 10) and repetition of steps 2-10—The coding DNA strand prepared above (approximately 100 pmol, stored as dried pellet) was ligated to FS1 as follows:

100 pmol of FS1 was phosphorylated in 50 µL reaction volume with 10 µCi [γ-32P]ATP and 10 units of PNK for 10 min at 37° C. followed by the addition of non-radioactive ATP (1 µL from 50 mM stock, 1 mM final concentration) and incubation for another 20 min at 37° C. Note: for the remaining selection rounds, the reaction volume of phosphorylation of FS1 was constantly maintained at 50 µL. After quenching the reaction by heating at 90° C. for 5 min, the reaction mixture was transferred to the dried purified PCR products obtained from the step 9.

Approximately 110 pmol of RFT1 was added to this solution. The mixture was heated at 90° C. for 40 s and cooled to room temperature for 10 min. Then, 10 µL of T4 DNA ligase buffer was added and the volume of the reaction was adjusted to 100 µL with ddH2O. The ligation reaction was initiated by adding 10 units of T4 DNA ligase and continued for 2 h. After purification by 10% dPAGE, the ligated DNA product was used for the second round of selection using the same procedure as described for the first round.

A total of 20 cycles of selection were conducted; the percentage of cleaved RFL1 in step 6 in each cycle is depicted in FIG. 1B. The DNA population from round 20 was cloned and sequenced.

The DNA library was incubated in the selection buffer (SB; 50 mM HEPES, pH 7.5, 150 mM NaCl, 15 mM MgCl2, and 0.01% Tween 20) for 5 h, followed by 1-h incubation with CEM-BS diluted with 2×SB at 1:1 ratio—this combined procedure served as the "negative selection" step to remove any self-cleaving and non-specific DNAzymes. The uncleaved DNA molecules were purified by 10% denaturing polyacrylamide gel electrophoresis (dPAGE) and then incubated with CEM-EC in 1×SB for 30 min. This was the positive selection step designed to isolate fluorescent DNAzymes that can specifically respond to CEM-EC. The cleaved DNA sequences were purified by dPAGE, amplified by polymerase chain reaction (PCR) and used for the next cycle of selective amplification. After 20 iterations (the selection progress is shown in FIG. 1B), a strong CEM-EC dependent cleavage activity was established (over 30% cleavage in the presence of CEM-EC, comparing to less than 1% cleavage with CEM-BS; see the inserted gel image in FIG. 1B).

The DNA pool from the 20th round was cloned and sequenced. Three classes of DNAzymes were discovered; the sequence of the most dominant signaling DNAzyme, named RFD-EC1, is provided in FIG. 3A. The activity of synthetically produced RFD-EC1 was examined using fluorescence assay (FIG. 3B) and dPAGE analysis (FIG. 3C). A scrambled sequence, RFSS1 (its sequence is shown in FIG. 3A) was tested as a control.

For fluorescence based assay measured in a fluorimeter, CEM-EC and 2×SB were mixed at 1:1 ratio in a quartz crystal cuvette; such a solution maintained a steady level of fluorescence (see the constant level of fluorescence in the initial 5 min of the fluorescence plot in FIG. 3B). However, the addition of RFD-EC1 (final concentration of 100 nM) to this solution caused dramatic time-dependent increase in fluorescence (FIG. 3B; data in black). In contrast, no significant fluorescence increase was observed for RFSS1 (FIG. 3B; the initial fluorescence increase upon the addition of RFSS1 was attributed to the background fluorescence of the fluorogenic signaling module because the florescence from the fluorescein was not completely quenched by dabcyl).

To verify that the fluorescence increase of RFD-EC1 was indeed due to the cleavage of the RNA linkage, the cleavage reaction was also analyzed by 10% dPAGE. The cleavage of RFD-EC1 was expected to generate two DNA fragments; the 5'-cleavage fragment retains the fluorophore and can be detected by fluorescence imaging while the 3'-fragment does not fluoresce (see the marker lane in FIG. 3C; it was a sample of RFD-EC1 after treatment with 0.25N NaOH for 20 h at room temperature, a procedure that is known to cause the full cleavage of RNA[11]). The results presented in FIG. 3C are consistent with this prediction: RDF-EC1 cleaved itself in the presence of CEM-EC but not in SB alone (labelled as "NC", negative control). In contrast, RFSS1/CEM-EC mixture only produced an extremely weak cleavage band.

Next, the response of RFD-EC1 to CEM produced by other microbes was investigated. Nine gram negative bacteria (in addition to *E. coli*) and 5 gram-positive bacteria (including *B. subtilis*, whose CEM was used during the negative selection step) were chosen for this experiment; the full names of all these bacteria can be found in the legend of FIG. 4.

For this experiment, each bacterium was cultured in LB for a different period of time (because these bacteria have varying growth rates in LB) until the OD600 (optical density at 600 nm) of each cell culture reached ~1. The CEM was then obtained and used to induce the cleavage of RFD-EC1 in a 1-h reaction.

None of the CEMs from these arbitrarily chosen bacteria (FIG. 4A) was able to activate RFD-EC1. This experiment indicates that this DNAzyme is highly specific to the CEM of *E. coli*.

To investigate the nature of the targets (proteins or small molecules) in the CEM-EC that activate RDF-EC1, the CEM-EC was treated with two proteases, trypsin (TS) and proteinase K. It was found that the CEM-EC treated with either protease was no longer able to activate RFD-EC1 (FIG. 3B).

Without being bound by theory, these observations suggest that the likely target for the DNAzyme activation is a protein.

To examine whether the observed cleavage activity of RFD-EC1 was simply caused by possible RNases that may exist in the CEM-EC, two tests were carried out. In the first test, Ribolock (RI RNase inhibitor, was added into the CEM-EC. As shown in FIG. 3C, the addition of RI did not impact the activity of RFD-EC1 (see the lane labelled as "CEM-EC/RI"). In the second test, the cleavage reaction was conducted in presence of 100-fold excess tRNA (transfer ribonucleic acid from baker's yeast, obtained from Sigma-Aldrich). This treatment also did not cause any reduction to the cleavage activity of RFD-EC1 (see the sample labelled as "CEM-EC/tRNA" in FIG. 4C).

These results, along with the previous observation that RFSS1 (mutated RFD-EC1) failed to cleave upon contacting CEM-EC (FIG. 3), strongly suggest that the cleavage of RFD-EC1 was not simply caused by an RNase.

Next, an experiment to probe into the possible molecular weight of the target using molecular sizing column (NANOSEP OMEGA, Pall Incorporation) was carried out. CEM-EC was passed through several centrifugal columns with a cut-off molecule weight of 3K (3,000 Daltons), 10K, 30K, 50K and 100K, respectively. It was found that while the 3K, 10K and 30K filtrates of CEM-EC did not induce the cleavage of RFD-EC1, the filtrates from both 50K and 100K spin columns contained the target (FIG. 4D).

Without being bound by theory, these results suggest that the potential protein target may have a molecular weight between 30,000 and 50,000 Daltons.

Detection of Bacterial Cells

The ability to detect a single live cell is a hallmark of a bacterial detection method for many practical applications such as detection of food-borne pathogens[1]. For this reason, bacterial detection methods in such practices have an essential cell-culturing step. This method has an integrated cell-culturing step and is expected to offer the capability for single live cell detection. To verify this, the experiment described next was carried out.

First, using culture plating method as detailed in SI, 4 *E. coli* stocks were prepared containing 20, 2, 0.2 and 0.02 colony-forming units (CFUs; 1 CFU=a single live cell) per 100 µL; these stocks were labeled as Stocks A-D, respectively. From each stock, 15×100 µL were taken to inoculate 15 parallel solutions of LB. Theoretically the individual tube inoculated with Stocks A, B, C and D would contain an average of 20, 2, 0.2 and 0.02 CFUs, respectively. Thus bacterial growth in all the tubes inoculated with Stocks A and B, 3 of the 15 tubes inoculated with Stock C (0.2×15=3), and none of the 15 tubes inoculated with Stock D (0.02×15=0.3≤1) was expected. All inoculated solutions were incubated at 37° C. for 24 h, CEM-EC was then prepared from each cell culture and used to activate the cleavage of RFD-EC1 in a 1-h reaction using dPAGE analysis.

The results from the experiment, shown in FIG. 5, are consistent with the expectation: CEM-EC from all Stock-A inoculations, all but one Stock-B inoculations, 2 (instead of 3) out of 15 Stock-C inoculations and none of Stock-D inoculations produced a cleavage band (note that OD600 of each positive culture was between 1.0 and 1.2 while that of each negative sample was negligible). These results demonstrate that the estimated CFUs for the stocks are quite accurate, and more importantly, the fluorogenic DNAzyme based method detects a single live cell (1 CFU).

The time required to generate a detectable signal if 1 CFU of *E. coli* was used to initiate cell growth was also investigated. From the data shown in FIG. 6A, a culturing time of 12 h was needed to achieve a robust signal, although a weak signal was observed following 8-h culturing.

Finally, the number of seeding cells required to produce CEM-EC, after 6-h cell culturing, that was concentrated enough to induce a detectable signal of RFD-EC1 was examined; the data is provided in FIG. 6B. This experiment revealed that when the culturing time was set to be 6 h, only ~500 cells were required to produce sufficiently concentrated CEM to induce the cleavage of RFD-EC1 that was significantly above background.

Example 2

Optimization of a Fluorogenic DNAzyme Based Assay for Bacterial Detection

As described above, an RNA-cleaving fluorescent DNAzyme (RFD) that reports the presence of a specific bacterium by interacting with the crude extracellular mixture (CEM) generated by this organism as cells proliferate has been created. This DNAzyme cleaves its substrate at a lone RNA linkage (R) embedded in a DNA chain and flanked by nucleotides labeled with a fluorophore (F) and a quencher (Q). In this study, the performance of the assay was improved by optimizing target sample preparation procedures, bacterial growth and DNAzyme reaction conditions.

(A) Cleavage Performance of the DNAzyme in Trans

Cleavage performances of the DNAzyme in cis (where the substrate is directly linked to the enzyme) and in trans (where the DNAzyme and the substrate exist separately) were tested. Cleavage performance of constructs EC1 (a full length DNAzyme including primer binding sites previously obtained from the in vitro selection; SEQ ID NO: 1), EC1T (a truncated version of EC1 after the primer binding sites), and EC1TM were tested in trans-acting form (where the DNAzyme and the substrate exist separately) (FIG. 7). A sensitivity test of EC1T in trans-acting form with varying numbers of *E. Coli* cells is shown in FIG. 8. The trans DNAzyme afforded a detection limit of $10^4$ CFUs and detects a single bacterium in 6 hrs by gel electrophoresis (FIG. 9). Similar tests with cis-acting EC1 are shown in FIGS. 10 and 11.

Methods

Preparation of cis-Acting EC1-FS1:

cis-acting EC1-FS1 construct was generated by template mediated enzymatic ligation of FS1 to EC1. In brief, 200 pmol of FS1 was phosphorylated in 50 uL reaction volume 1 mM ATP concentration and 20 U of PNK for 30 min at 37° C. in 1×PNK buffer A. The reaction was quenched by heating at 90° C. for 5 min and cooled down to room temperature for 10 min. Equimolar EC1 and EC1 LT (ligation template) were then added to this solution, heated at 90° C. for 30 s and cooled to room temperature for 10 min. Afterwards, 10 µL of 10×T4 DNA ligase buffer (buffer info as for PNK) was added and the volume was adjusted to 100 µL with ddH$_2$O. This was followed by the addition of 10 units of T4 DNA ligase and incubation at room temperature for 2 h. The reaction was then quenched by adding 10 µL of NaOAc (3 M, pH 7.0) and 250 µL of cold 100% ethanol. After mixing the mixture was placed at −20° C. for an hour. After ethanol precipitation, the DNAzyme was purified by 10% dPAGE.

DNAzyme Activity Assays in Trans:

Cleavage performance of constructs EC1, EC1T, and EC1TM were tested in trans-acting form. Two reaction mixtures for each construct were prepared; one as control where the reaction was conducted with the TSB and RB only excluding CEM-EC, the second one was test. The first, for the control experiment 23 µL of TSB was taken in a microcentrifuge tube followed by 25 µL of 2×RB, 1 µL of 2.5 µM FS1 and 1 µL of 25 µM of each construct in individual tube. For the test, reaction mixture was prepared similarly except adding 23 µL of CEM-EC instead of TSB. Each mixture was then incubated at room temperature for 60 min and then quenched by adding 5 µL of NaOAc (3 M) and 135 µL of ethanol (100%). After ethanol precipitation, the DNA molecules were analyzed by 10% dPAGE. Fluorescent DNA bands were visualized by fluorimager (Typhoon 9200, GE Healthcare).

(B) Target Accumulation in Intracellular Mixture

Figure 12:
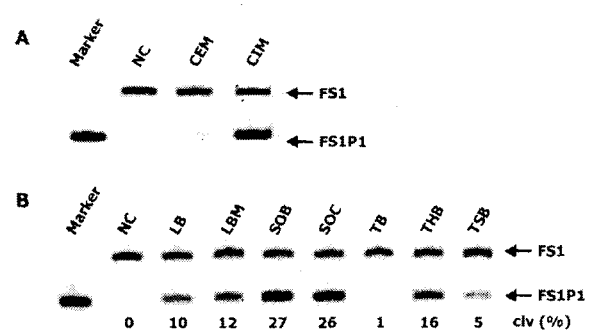

The target protein accumulated in the CEM of *E. coli* can also be found in its crude intracellular mixture (CIM) and could be rescued with a quick centrifugation of cells and mild heat treatment to induce the release of CIM (FIG. 12). It was shown that the target that activates the DNAzyme has a higher concentration intracellularly than extracellularly and that different growth media produces different amounts of target.

Methods

Preparation of Bacterial Crude Mixtures:

E. coli was plated onto a tryptic soy agar (1.5%) and grown for 14 h at 37° C. A single colony was picked and inoculated in 2 mL of TSB and grown for 14 h (overnight) at 37° C. with shaking at 250 rpm. Afterwards, a 1% re-inoculation was prepared by taking 20 µL of the overnight culture and transferring to a fresh 2 mL of TSB. The re-inoculation was grown at 37° C. with shaking at 250 rpm until the culture reached on $OD_{600}$ (optical density at 600 nm) of ~1. Crude extracellular mixture (CEM) was prepared by separating cells from 1 mL of the culture with centrifugation at 11,000 g for 5 min at room temperature. The crude supernatant was then collected fresh in microcentrifuge tubes and stored at −20° C. Crude intracellular mixtures (CIMs) were extracted by re-suspending cell pellets in 200 µL of 1× reaction buffer (RB; 50 mM HEPES, 150 mM NaCl, 15 mM $MgCl_2$ at pH 7.5) and heating at 50° C. for 15 min. The heat treated cell suspension was then centrifuged at 11,000 g for 5 min at room temperature. The clear supernatant was transferred to a fresh microcentrifuge tube and stored at −20° C.

CIMs collected from bacteria other than E. coli listed above were prepared in a similar manner except each species was cultured in SOB for a different length of time (because each bacterium possess a different growth rate) until each culture reached an $OD_{600}$ of ~1.

CEM-EC and CIM-EC Activity Assay:

100 µL of a prepared 50000 CFU/mL glycerol stock was inoculated in 2 mL of TSB and grown at 37° C. for 7 h with shaking at 250 rpm. CEM and CIM were prepared similarly as described above, except the CIM was extracted in 100 µL of 1×RB. The CEM reaction consisted of 20 µL of CEM-EC, 25 µL of 2×RB, 1 µL of 2.5 µM FS1, 1 µL of 25 µM of EC1T and 3 µL $ddH_2O$. The CIM reaction was prepared with 20 µL of CIM-EC, 28 µL of 1×RB, 1 µL of 2.5 µM FS1 and 1 µL of 25 µM of EC1T. Each reaction was then incubated at room temperature for 60 min, ethanol precipitated and analyzed by 10% dPAGE as before (FIG. 12A).

Cleavage Assay with CIMs Collected from E. Coli Grown in Various Growth Media:

100 µL of a prepared 2500 CFU/mL glycerol stock was inoculated in 2 mL of LB, LBM, SOB, SOC, TB, TH or TSB. Each culture was allowed to grow for 7 h and 1 mL was then centrifuged and subjected to CIM extraction in 50 µL 1×RB (as described previously). Reaction mixtures were then set-up with 25 µL of CIM-EC, 23 µL of 1×RB, 1 µL of 2.5 µM FS1 and 1 µL of 25 µM of EC1T as described above. After 60 min incubation at room temperature, mixtures were ethanol precipitated and analyzed by 10% dPAGE (FIG. 12B).

(C) Co-Factor, Temperature and pH

Figure 13:
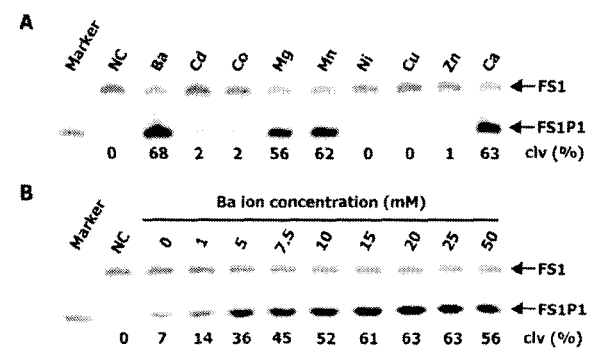

It was found that several metal ions (Ba, Mg, Mn and Ca) can support the DNAzyme activity (FIG. 13). Under some conditions, $Ba^{2+}$ may be a more efficient metal ion cofactor for the DNAzyme than the original $Mg^{2+}$ used during the original in vitro selection process. The DNAzyme exhibits an optimal activity at room temperature and shows a broad pH (5-8) profile (FIG. 14).

Methods

Activity of EC1T with Different Divalent Metals:

Reaction mixtures were prepared to a final volume of 50 µL containing 25 µL 2×RB without $MgCl_2$ (100 mM HEPES, 300 mM NaCl at pH 7.5), 5 µL of 150 mM $M^{2+}$ ($BaCl_2$, $CdCl_2$, $CoCl_2$, $MgCl_2$, $MnCl_2$, $NiCl_2$, $CuCl_2$, $ZnCl_2$, and $CaCl_2$), 1 µL of 2.5 µM FS1, 1 µL of 25 µM EC1T and 15.5 µL of $ddH_2O$. Finally, 2.5 µL CIM-EC was added and the reaction was incubated at room temperature for 60 min. Reactions were then quenched, ethanol precipitated and analyzed by 10% dPAGE as before (FIG. 13A). Negative control experiments were conducted with RB, FS1 and EC1T only omitting divalent metal ions.

$BaCl_2$ was used as the $M^{2+}$ of choice and was subsequently titrated from 0 to 50 mM (final concentration) in the reaction mixture with EC1T, FS1 and CIM-EC as prepared before. Briefly, 1, 5, 7.5, 10, 15, 20 and 25 mM reactions were prepared by adding 0.5, 2.5, 3.75, 5, 7.5, 10, and 12.5 µL of 100 mM $BaCl_2$, respectively, and a 50 mM reaction was prepared by adding 2.5 µL of 1 M $BaCl_2$ to reaction mixtures containing 25 µL 2×RB without any $M^{2+}$, 1 µL of 2.5 µM FS1, 1 µL of 25 µM EC1T. Volumes were then adjusted by adding the appropriate difference in $ddH_2O$. Each reaction was mixed by and pipetting. Finally, 2.5 µL CIM-EC was added and the reaction was incubated at room temperature for 60 min. Reactions were then quenched, ethanol precipitated and analyzed by 10% dPAGE as before (FIG. 13B).

Reaction Temperature Dependence:

In order to find out the optimal reaction temperature, reaction cleavage reactions carried out at different temperature such as 4, 15, 23, 37 and 50° C. A 50 µL reaction volume containing 25 µL 2×RB with $BaCl_2$ (30 mM), 1 µL of 2.5 µM FS1, 1 µL of 25 µM EC1T and 20.5 µL of $ddH_2O$ was set up. Two sets of reactions were prepared for each temperature, a control sample to which 2.5 µL of $ddH_2O$ was added instead of CIM and a test sample to which 2.5 µL of CIM-EC was added. Reactions were incubated for 60 min at their respective temperatures and then ethanol precipitated and analyzed by 10% dPAGE (FIG. 14B).

pH Dependence:

A DNAzyme pH profile was tested by preparing 2×RB solutions using different chemical compounds for each respective pH. RB's for pH 5.0, 5.5 and 6.0 were prepared with 100 mM MES, 300 mM NaCl and 30 mM $BaCl_2$, RB's for pH 6.5, 7.0, 7.5 and 8.0 were prepared with 100 mM HEPES, 300 mM NaCl and 30 mM $BaCl_2$ and RB's for pH 8.5 and 9.0 were prepared with 100 mM Tris-HCl, 300 mM NaCl and 30 mM $BaCl_2$. Cleavage reactions procedures, dPAGE analysis were same as described for temperature dependency (FIG. 14C).

Optimizing the Substrate and DNAzyme Ratio (FS1:EC1T):

Substrate DNAzyme (FS1:EC1T) ratios 1:0, 1:1, 1:2, 1:5, 1:10, 1:25, 1:50, and 1:100 were tested for greatest cleavage activity. Firstly, A 50 µL reaction volume containing 25 µL of 2×RB (100 mM HEPES, 300 mM NaCl and 30 mM $BaCl_2$, pH 7.5) and 1 µL of 2.5 µM FS1 was prepared. Ratios 1:1, 1:2 and 1:5 were prepared by adding 1, 2 and 5 µL of 2.5 µM EC1T, respectively. Ratios 1:10, 1:25 and 1:50 were prepared by adding 1, 2 and 5 µL of 25 µM EC1T, respectively. Finally, ratio 1:100 was prepared by adding 2.5 µL of 100 µM EC1T. Final volumes were adjusted as required with $ddH_2O$. All reactions included a control and test sample for ratio and were incubated for 60 min at room temperature. Mixtures were then ethanol precipitated and analyzed by 10% dPAGE.

Example 3

DNAzyme Probes for Listeria monocytogenes and Salmonella Typhimurium

DNAzyme probes were generated for the bacterial pathogens Listeria monocytogenes and Salmonella typhimurium using the methods described herein.

LM-RFD (SEQ ID NO: 3) is a DNAzyme isolated for *L. monocytogenes* and ST-RFD (SEQ ID NO: 4) is a DNAzyme isolated for *S. typhimurium*.

The signalling properties of the *L. monocytogenes* and *S. typhimurium*-specific probes are shown in FIG. 15. The *L. monocytogenes* and *S. typhimurium*-specific probes are highly specific in the presence of other pathogenic (FIG. 16) and non-pathogenic (FIG. 17) bacteria.

The *L. monocytogenes* and *S. typhimurium*-specific probes are highly sensitive as shown in FIG. 18 and able to detect of *L. monocytogenes* and *S. typhimurium*, respectively, from a mixed culture (FIG. 19).

FIG. 20 shows the detection of a live single cell of *L. monocytogenes* (A and B) and *S. typhimurium* (C and D) in a food sample. FIG. 21 shows the effect of hot dog in target excretion by the *S. typhimurium* specific DNAzyme.

REFERENCES

[1] M. Zourob, S. Elwary, A. Turner, Principles of Bacterial Detection: Biosensors, Recognition Receptors and Microsystems, Springer, New York, 2008.

[2] a) V. Velusamy, K. Arshak, O. Korostynska, K. Oliwa, C. Adley, Biotechnol. Adv. 2010, 28, 232-254; b) O. Lazcka, F. J. D. Campo, F. X. Munoz, Biosens. Bioelectron. 2007, 22, 1205-1217; c) A. C. Wright, M. D. Danyluk, W. S. Otwell, Curr. Opin. Biotechnol. 2009, 20, 172-177; d) D. R. Call, Crit. Rev. Microbiol. 2005, 31, 91-99; e) K. Yagi, Appl. Microbiol. Biotechnol. 2007, 73, 1251-1258; f) I. Laberge, M. W. Griffiths, M. W. Griffiths, Int. J. Food Microbiol., 1996, 32, 1-26.

[3] a) N. K. Navani, Y. Li, Curr. Opin. Chem. Biol. 2006, 10, 272-281; b) J. Liu, Z. Cao, Y. Lu, Chem. Rev. 2009, 109, 1948; c) Y. Li, Y. Lu, Functional Nucleic Acids for Analytical Applications, Springer, New York, 2009; d) X. Fang, W. Tan, Acc. Chem. Res. 2010, 43, 48-57.

[4] a) R. R. Breaker, G. F. Joyce, Chem. Biol. 1994, 1, 223-229; b) B. Cuenoud, J. W. Szostak, Nature 1995, 375, 611-614; c) D. J. Chinnapen, D. Sen, Proc. Natl. Acad. Sci. U.S.A. 2004, 101, 65-69; d) K. Schlosser, Y. Li, Chem. Biol. 2009, 16, 311-322; e) S. K. Silverman, Angew. Chem. Int. Ed. 2010, 49, 7180-7201.

[5] a) C. Tuerk, L. Gold, Science 1990, 249, 505-510; b) A. D. Ellington, J. W. Szostak, Nature 1990, 346, 818-822; c) G. F. Joyce, Angew. Chem. Int. Ed. 2007, 46, 6420-6436.

[6] a) J. Liu, Y. Lu, J. Am. Chem. Soc. 2004, 126, 12298-12305; b) J. Liu, Y. Lu, Angew. Chem. Int. Ed. 2007, 46, 7587-90; c) M. Hollenstein, C. Hipolito, C. Lam, D. Dietrich, D. M. Perrin, Angew. Chem. Int. Ed. 2008, 47, 4346-4350; d) J. Elbaz, O. Lioubashevski, F. Wang, F. Remacle, R. D. Levine, I. Willner, Nat. Nanotechnol. 2010, 5, 417-22; e) K. Lund, A. J. Manzo, N. Dabby, N. Michelotti, A. Johnson-Buck, J. Nangreave, S. Taylor, R. Pei, M. N. Stojanovic, N. G. Walter, E. Winfree, H. Yan, Nature 2010, 465, 206-210.

[7] a) S. H. Mei, Z. Liu, J. D. Brennan, Y. Li, J. Am. Chem. Soc. 2003, 125, 412-420; b) Z. Liu, S. H. Mei, J. D. Brennan, Y. Li, J. Am. Chem. Soc. 2003, 125, 7539-7545.

[8] a) S. A. Kandadai, Li, Y., Nucleic Acids Res. 2005, 33, 7164-7175; b) Y. Shen, J. D. Brennan, Y. Li, Biochemistry 2005, 44, 12066-12076; c) W. Chiuman, Y. Li, J. Mol. Biol. 2006, 357, 748-754; d) W. Chiuman, Y. Li, Chem. Biol. 2006, 13, 1061-1069; e) M. M. Ali, Kandadai, S. A., Li, Y. Can. J. Chem. 2007, 85, 261-273; f) W. Chiuman, Y. Li, PLoS One 2007, 2, e1224; g) S. A. Kandadai, W. W. Mok, M. M. Ali, Y. Li, Biochemistry 2009, 48, 7383-7391.

[9] a) Y. Shen, W. Chiuman, J. D. Brennan, Y. Li, ChemBioChem 2006, 7, 1343-1348; b) N. Rupcich, W. Chiuman, R. Nutiu, S. H. Mei, K. K. Flora, Y. Li, J. D. Brennan, J. Am. Chem. Soc. 2006, 128, 780-790; c) Y. Shen, G. Mackey, N. Rupcich, D. Gloster, W. Chiuman, Y. Li, J. D. Brennan, Anal. Chem. 2007, 79, 3494-3503.

[10] M. M. Ali, Y. Li, Angew. Chem. Int. Ed. 2009, 48, 3512-3515.

[11] Y. Li, R. R. Breaker, J. Am. Chem. Soc. 1999, 121, 5364-5372.

We claim:

1. A catalytic nucleic acid probe for detecting a microorganism, wherein the catalytic nucleic acid probe is a single nucleic acid molecule that comprises (a) a first nucleic (i) interacts with a microorganism protein target and (ii) has catalytic activity to cleave a detectable substrate upon interaction with the protein target, thereby generating a detectable signal and (b) a second nucleic acid region comprising the detectable substrate.

2. The catalytic nucleic acid probe of claim 1, wherein the detectable substrate is a single ribonucleotide linkage embedded in a DNA sequence and the ribonucleotide linkage is directly flanked by a fluorophore modified nucleic acid residue on one side and a quencher modified nucleic acid residue on the other side such that the fluorophore is quenched until the ribonucleotide linkage is cleaved, thereby generating a fluorogenic signal.

3. The catalytic nucleic acid probe of claim 1, wherein the catalytic nucleic acid probe comprises SEQ ID NO: 1, SEQ ID NO: 2, SEQ ID NO: 3, SEQ ID NO: 4 or residues 1-99 of SEQ ID NO: 15.

4. The catalytic nucleic acid probe of claim 1, wherein the catalytic nucleic acid probe comprises a sequence with at least 80% sequence identity to SEQ ID NO: 5.

5. The catalytic nucleic acid probe of claim 1, wherein the nucleic acid probe comprises (a) a sequence with at least 80% sequence identity to any one of SEQ ID NO: 1, SEQ ID NO: 2, SEQ ID NO: 3, SEQ ID NO: 4 and residues 1-99 of SEQ ID NO: 15 and (b) a sequence with at least 80% sequence identity to SEQ ID NO: 5.

6. A method of detecting a microorganism in a sample comprising:
exposing the sample to the catalytic nucleic acid probe of claim 1, wherein the catalytic nucleic acid probe (i) interacts with the microorganism protein target and (ii) cleaves the detectable substrate upon interaction of the catalytic nucleic acid probe with the protein target thereby generating the detectable signal that indicates the presence of the microorganism in the sample.

7. The method of claim 6, wherein the detectable substrate is a single ribonucleotide linkage embedded in a DNA sequence and the ribonucleotide linkage is directly flanked by a fluorophore modified nucleic acid residue on one side and a quencher modified nucleic acid residue on the other side such that the fluorophore is quenched until the ribonucleotide linkage is cleaved, thereby generating a fluorogenic signal.

8. The method of claim 6, wherein a single colony forming unit of the microorganism is detected.

9. The method of claim 6, wherein the microorganism is a bacterial pathogen.

10. The method of claim 6, wherein the bacterial pathogen is selected from the group consisting of *E. coli, L. monocytogenes* and *S. typhimurium*.

11. The catalytic nucleic acid probe of claim 1, wherein the catalytic nucleic acid probe comprises a sequence with at least 80% sequence identity to any one of SEQ ID NO: 1, SEQ ID NO: 2, SEQ ID NO: 3, SEQ ID NO: 4 or residues 1-99 of SEQ ID NO: 15.

12. The catalytic nucleic acid probe of claim 1, wherein the catalytic nucleic acid probe comprises a sequence with at least 95% sequence identity to any one of SEQ ID NO: 1, SEQ ID NO: 2, SEQ ID NO: 3, SEQ ID NO: 4 or residues 1-99 of SEQ ID NO: 15.

13. The catalytic nucleic acid probe of claim 1, wherein the catalytic nucleic acid probe comprises a sequence with at least 95% sequence identity to SEQ ID NO: 5.

14. The catalytic nucleic acid probe of claim 1, wherein the catalytic nucleic acid probe is generated by contacting a plurality of candidate nucleic acid molecules with the microorganism protein target, wherein each of the candidate nucleic acid molecules comprises a variable region of nucleic acid sequence and selecting the catalytic nucleic acid probe from the plurality of the candidate nucleic acid molecules that (i) interacts with the microorganism protein target and (ii) has catalytic activity to cleave the detectable substrate upon interaction with the microorganism protein target.

15. The catalytic nucleic acid probe of claim 2, wherein the fluorophore is fluorescein, the ribonucleotide is ribo-A and the quencher is dabcyl.

16. A kit for detecting a microorganism, wherein the kit comprises the catalytic nucleic acid probe of claim 1 and instructions for use of the kit for detecting a microorganism.

17. The method of claim 6, wherein the sample is a food sample, a medical sample, a water sample or an environmental sample.

\* \* \* \* \*

UNITED STATES PATENT AND TRADEMARK OFFICE
CERTIFICATE OF CORRECTION

PATENT NO. : 9,624,551 B2
APPLICATION NO. : 14/003645
DATED : April 18, 2017
INVENTOR(S) : Yingfu Li, M. Monsur Ali and Sergio D. Aguirre Page 1 of 1

It is certified that error appears in the above-identified patent and that said Letters Patent is hereby corrected as shown below:

In the Claims

Claim 1, Line 4-5, Column 31, "nucleic (i) interacts" should read as --nucleic acid region that (i) interacts--

Signed and Sealed this
Twenty-ninth Day of October, 2019

Andrei Iancu
*Director of the United States Patent and Trademark Office*